(12) United States Patent
Velazquez et al.

(10) Patent No.: US 8,440,617 B2
(45) Date of Patent: May 14, 2013

(54) HYPERBARIC TREATMENT IN WOUND HEALING

(75) Inventors: Omaida C. Velazquez, Bryn Mawr, PA (US); Katherine A. Gallagher, Ellicott City, MD (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 202 days.

(21) Appl. No.: 12/532,422

(22) PCT Filed: Mar. 21, 2008

(86) PCT No.: PCT/US2008/003760
§ 371 (c)(1),
(2), (4) Date: May 24, 2010

(87) PCT Pub. No.: WO2008/118370
PCT Pub. Date: Oct. 2, 2008

(65) Prior Publication Data
US 2010/0272684 A1    Oct. 28, 2010

Related U.S. Application Data

(60) Provisional application No. 60/907,147, filed on Mar. 22, 2007.

(51) Int. Cl.
*A61K 38/19* (2006.01)
*A61P 17/02* (2006.01)
*C07K 14/52* (2006.01)

(52) U.S. Cl.
USPC ............... 514/9.4; 514/13.3; 514/18.6

(58) Field of Classification Search ............ None
See application file for complete search history.

(56) References Cited

U.S. PATENT DOCUMENTS

| | | | |
|---|---|---|---|
| 6,720,340 B1 * | 4/2004 | Cooke et al. | 514/343 |
| 2004/0258669 A1 | 12/2004 | Dzau et al. | |
| 2006/0105950 A1 * | 5/2006 | Losordo | 514/12 |
| 2006/0110374 A1 * | 5/2006 | Czeiger et al. | 424/93.7 |
| 2006/0201504 A1 * | 9/2006 | Singhal et al. | 128/204.18 |
| 2009/0304636 A1 * | 12/2009 | Zsebo | 424/93.2 |
| 2009/0311223 A1 * | 12/2009 | Ichim | 424/93.7 |

OTHER PUBLICATIONS

Aicher et al., Nat. Med. 2003; 11 : 1370-1376.*
Sefton, "Implantable Pumps", CRC Crit. Ref. Biomed. Eng. 14:201 (1987).
Buchwald et al., "Long-term, continuous intravenous heparin administration by an implantable infusion pump in ambulatory patients with recurrent venous thrombosis" Surgery 88:507 (1980).
Saudek et al., "A preliminary trial of the programmable implantable medication system for insulin delivery", N. Engl. J. Med. 321:574 (1989).
Goodson, "Dental Applications", in Medical Applications of Controlled Release, supra, vol. 2, pp. 115-138 (1984).
Langer, "New Methods of Drug Delivery", Science 249:1527-1533 (1990).
Askari et al., "Effect of stromal-cell-derived factor 1 stem cell homing and tissue regeneration in ischaemic cardiomyopathy", The Lancet, vol. 362, issue 9385, 2003, pp. 697-703.
Aicher et al., "Essential role of endothelial nitric oxide synthase for mobilization of stem and progenitor cells", Nat. Med. 2003; 11: pp. 1370-1376.

* cited by examiner

*Primary Examiner* — Daniel C Gamett
(74) *Attorney, Agent, or Firm* — Mark S. Cohen; Pearl Cohen Zedek Latzer, LLP

(57) ABSTRACT

This invention relates to methods for treating chronic dermal ulcers using hyperbaric treatment in combination with progenitor cells and chemokine homing factors. Specifically, the invention relates to treatment of chronic wounds resulting from diabetes mellitus using compositions comprising EPC and SDF-1A, under hyperbaric condition to accelerate wound healing.

8 Claims, 27 Drawing Sheets

C

DIABETIC + SDF-1α　　　　NONDIABETIC

D

A

B

HYPERBARIC TREATMENT IN WOUND HEALING

CROSS-REFERENCE TO RELATED APPLICATIONS

This application is a National Phase Application of PCT International Application PCT/US08/03760, filed Mar. 21, 2008, priority to United States Provisional Patent Application 60/907,147, filed Mar. 22, 2007, which is incorporated by reference herein in it's entirety.

GOVERNMENT INTEREST

This invention was supported, in part, by Grant Number 1-R01-DK071084 and K-01-HL073145 from the NIH. The government may have certain rights in the invention.

FIELD OF INVENTION

This invention is directed to methods for treating chronic dermal ulcers using hyperbaric treatment in combination with progenitor cells and chemokine homing factors. Specifically, the invention relates to treatment of chronic wounds resulting from diabetes mellitus using compositions comprising EPC and SDF-1A, under hyperbaric condition to accelerate wound healing.

BACKGROUND OF THE INVENTION

Diabetes mellitus encompasses a range of conditions characterized by an elevation of blood glucose level, and is divided into two principal varieties. Type 1 accounts for less than 10% of all diabetics and is due to an autoimmune attack on the pancreatic β-cells that results in their destruction. Type 2 diabetics exhibit impairments of both insulin secretion and insulin action. Type 2 diabetes has reached epidemic proportions in Western societies, and is predicted to affect 300 million people worldwide by 2025. Nearly 800,000 new cases of diabetes mellitus are diagnosed per year in the United States, and approximately 15% of patients will develop a lower extremity ulceration at some point in their lives. It has been estimated that up to 2 million Americans suffer from non-healing lower extremity wounds, accounting for 162,500 annual hospitalizations and one billion dollars per year in health care costs in the United States.

The pathophysiology of diabetic lower extremity ulcerations and delayed healing has been well described. Contributing factors include progressive development of asensory, vasomotor and autonomic neuropathy leading to loss of protective sensation, joint and bone deformities that increase plantar foot pressure, and alterations in autoregulation of dermal blood flow. Diabetics show earlier development and progression of lower extremity peripheral arterial occlusive disease (PAD) with a predilection for the trifurcation level of vessels just distal to the knee. In addition, the tissue microcirculation is severely diseased (microangiopathy) even in patients with patent proximal vessels. Some of these vascular complications as well as the healing defects, in diabetes, have been associated with a decrease in number and function of circulating BMD EPC. Impaired host responses to infection and other cellular dysfunctions also contribute to the refractory nature of diabetic wounds. About 20% of diabetic lower extremity ulcers have arterial flow insufficiency as their primary etiology, approximately 50% will have primary diabetic neuropathy, and about 30% will have both conditions.

Despite a multidisciplinary approach (associating glycemia control, daily local care, foot off-loading antibiotic therapy, and surgical revascularization), treatment of diabetic ulcers is often prolonged, intensive and costly and treatment failures are common. Current approaches include debridement, frequent changes of wound dressing, specially fitted footwear, oral or intravenous antibiotics, complete bed rest, lengthy hospitalization and surgical revascularization. Ulcer-related complications can in some cases require amputation. Therefore, there is a need for treatments which accelerate the rate of the healing of chronic dermal skin ulcers in general, and of diabetic ulcers, in particular.

SUMMARY OF THE INVENTION

In one embodiment, the invention provides a method of increasing endothelial progenitor cell numbers (EPC) in a wound of a subject, comprising: mobilizing endothelial progenitor cells; and homing the endothelial progenitor cells into the wound, thereby increasing EPC numbers in a wound of a diabetic subject.

In another embodiment, the invention provides a method of accelerating a wound healing in a subject, comprising increasing release of endothelial progenitor cells from a bone marrow of said subject, and attracting the endothelial progenitor cells into the wound, thereby accelerating a wound healing in the subject.

In one embodiment, the invention provides a composition for accelerating a wound healing in a subject, comprising an endothelial progenitor cells (EPC) homing chemokine, its isomer, its metabolite, or a salt thereof, wherein said endothelial progenitor cells (EPC) homing chemokine attract endothelial progenitor cells into the wound, thereby accelerating wound healing.

In another embodiment, the invention provides a method of accelerating wound healing in a subject, comprising the step of increasing eNOS expression or function thereby increasing endothelial progenitor cells (EPC) release from bone marrow.

In one embodiment, the invention provides for the use of a compound that upregulates or activates SDF-1α, for accelerating wound healing in a subject.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which.

DETAILED DESCRIPTION OF THE INVENTION

Figure 1:
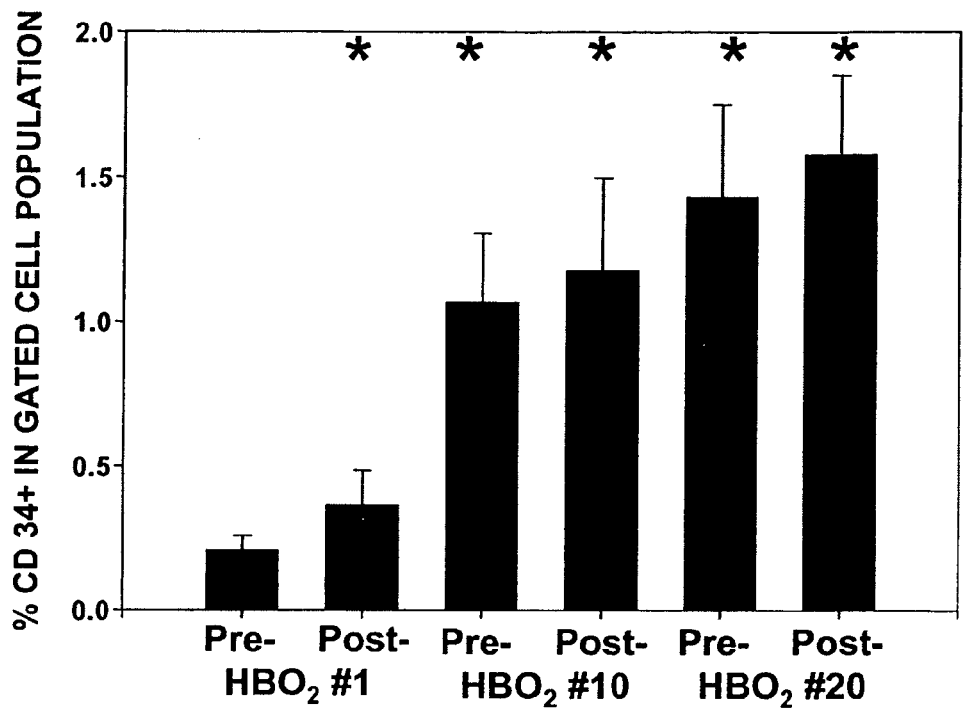
FIG. 1. shows mean CD34+ population in blood of humans before and after $HBO_2$ treatments. Data are the fraction of CD34+ cells within the gated population using leukocytes obtained from 26 patients before and after their $1^{st}$, $10^{th}$ and $20^{th}$ $HBO_2$ treatment. * Repeated measures one way analysis of variance, $p<0.05$ versus the pre-$HBO_2$ first treatment value.

This invention relates in one embodiment to methods for treating chronic dermal ulcers using hyperbaric, oxygen-enriched treatment in combination with progenitor cells and chemokine homing factors. In another embodiment, the invention relates to treatment of chronic wounds resulting from diabetes mellitus using compositions comprising EPC and SDF-1A, under hyperbaric condition to accelerate wound healing.

In one embodiment, contributing factors to aetiology of chronic diabetic wounds include progressive development of a sensory, or in another embodiment, vasomotor and autonomic neuropathy leading to loss of protective sensation, deformity that increases plantar foot pressure, and in certain other embodiments, alterations in autoregulation of dermal blood flow. In one embodiment, diabetics show earlier development and progression of lower extremity peripheral arterial occlusive disease with a predilection for the trifurcation level of vessels just distal to the knee. In another embodiment, the tissue microcirculation is severely diseased (microangiopathy) even in patients with patent proximal vessels. Impaired host response to infection and other cellular dysfunctions also contribute to the refractory nature of wound healing.

In one embodiment, normal wound healing proceeds through removal of necrotic debris and infection, resolution of inflammation, repair of the connective tissue matrix, angiogenesis, and resurfacing. In one embodiment, "problem" or "chronic" wounds refer to those wounds that fail to follow this sequence and do not achieve a sustained anatomic and functional result. In another embodiment, fibroblast recruitment, collagen deposition, angiogenesis and intracellular leukocyte bacterial killing are oxygen sensitive responses involved with normal wound healing. When hypoxia is pathologically increased in one embodiment, wound healing is impaired and the rate of wound infection increases. In another embodiment an essential part of normal healing is the formation of new vessels within the provisional wound matrix that is referred to as granulation tissue formation.

Neovascularization of wound granulation tissue occurs in one embodiment, by the processes of angiogenesis or in another embodiment, by vasculogenesis. The term "angiogenesis" refers in one embodiment, to the process by which resident endothelial cells of the wound's adjacent mature vascular network proliferate, and in other embodiments migrate, and remodel into neovessels that grow into the initially avascular wound tissue aided by mature stromal cells such as fibroblasts. In another embodiment, the term "vasculogenesis" refers to a de novo process by which EPC, recruited to the wound differentiate into endothelial cells and give rise to a replacement vascular network. In one embodiment, EPC has a critical role in ischemic wound healing. Accordingly and in one embodiment, the methods and compositions provided herein are used for stromageneis or in another embodiment collagen deposition or in another embodiment angiogenesis, or in another embodiment vasculogenesis in a wound, comprising administrating to the subject SDF-1α, or in another embodiment, stimulating eNOS release according to the methods provided herein. Each one of the vasculogenesis, or angiogenesis or stromageneis, or collagen deposition would be readily recognized by a person skilled in the art as a separate embodiment of the methods and compositions provided herein.

Accordingly and in one embodiment, provided herein is a method of increasing endothelial progenitor cell numbers (EPC) in a wound of a subject, comprising: mobilizing endothelial progenitor cells (EPC); and homing the endothelial progenitor cells (EPC) into the wound, thereby increasing EPC numbers in a wound of a diabetic subject.

In one embodiment, the term "progenitor cell", or "endothelial progenitor cells" or "EPC", refers to any somatic cell which has the capacity to generate fully differentiated, functional progeny by differentiation and proliferation. In another embodiment, progenitor cells include progenitors from any tissue or organ system, including, but not limited to, blood, nerve, muscle, skin, gut, bone, kidney, liver, pancreas, thymus, and the like. Progenitor cells are distinguished from "differentiated cells," which are defined in another embodiment, as those cells which may or may not have the capacity to proliferate, i.e., self-replicate, but which are unable to undergo further differentiation to a different cell type under normal physiological conditions. In one embodiment, progenitor cells are further distinguished from abnormal cells such as cancer cells, especially leukemia cells, which proliferate (self-replicate) but which generally do not further differentiate, despite appearing to be immature or undifferentiated.

Progenitor cells include in another embodiment, all the cells in a lineage of differentiation and proliferation prior to the most differentiated or the fully mature cell. Thus, in one embodiment, progenitors include the endothelial progenitor in the mature individual, which is capable of differentiation to only one type of cell, but which is itself not fully mature or fully differentiated. Production of mature, functional endothelial cells results from proliferation and differentiation of "unipotential progenitors," which in another embodiment, are those progenitors which have the capacity to make only that type of cell. In one embodiment, EPC are derived from bone marrow (BM).

In one embodiment, an uncommitted progenitor cell such as embryonic stem cell, is described as being "totipotent," i.e., both necessary and sufficient for generating all types of mature cells. Progenitor cells which retain a capacity to generate all pancreatic cell lineages but which can not self-renew are termed "pluripotent." In another embodiment, cells which can produce some but not all endothelial lineages and can not self-renew are termed "multipotent". In one embodiment, the methods provided herein further comprise administrating to the subject EPCs derived from ES cells. In another embodiment, SDF-1α. expression is increased in ES cells using the compositions described herein, which in one embodiment comprise an agent capable of up-regulating the expression of a nucleic acid encoding SDF-1α.

In one embodiment, phosphorylation of eNOS in bone marrow, (BM) is impaired in diabetic subjects and SDF-1α expression by stromal cells in the granulation tissue of cutaneous wounds is impaired as well. These two impairments directly impact in another embodiment mobilization of EPC from BM into circulation, and EPC-homing to wounds. In another embodiment these pathologies can be therapeutically reversed using the methods provided herein, to enhance EPCs available in peripheral wound tissue and improve wound healing. In one embodiment, HBO is used to induce tissue-level hyperoxia, thereby activating multiple BM NOS isoforms, leading in one embodiment to increased NO levels in the BM and hence, enhanced mobilization of EPCs into circulation, thus partially reversing the defect in eNOS activation and EPC release caused by diabetes.

In one embodiment, the term "homing" refers to the signals that attract and stimulate the cells involved in healing to migrate to sites of injury and aid in repair. EPC recruitment to the wound site depends in another embodiment, on ischemia-induced upregulation of stromal cell-derived factor-1α (SDF-1α). In one embodiment, the decreased expression of SDF-1α by epithelial cells and myofibroblasts is responsible for the lack of EPC homing to the periphery of diabetic wounds.

Hyperbaric oxygen therapy ($HBO_2$) refers in one embodiment to an adjunctive therapy used to stimulate wound healing in situations where the microvasculature has become attenuated. In another embodiment, patients receive 20 or more treatments breathing 100% $O_2$ in a pressurized chamber at between about 2.0 to about 3.2 atmospheres absolute (ATA), once or twice daily. In another embodiment, atmospheric pressure range from about 2 absolute atmospheres of pressure to about 3 absolute atmospheres of pressure. In one embodiment, atmospheric pressure range from about 2 absolute atmospheres of pressure to about 2.4 absolute atmospheres of pressure. Treatment time ranges in one embodiment, from about 10 minutes to about 240 minutes or in another embodiment the treatment time is about 10 minutes. In another embodiment, the treatment time is 15 minutes. In another embodiment, the treatment time is 30 minutes. In another embodiment, the treatment time is 60 minutes. In another embodiment, the treatment time is 90 minutes. In another embodiment, the treatment time is 120 minutes. In another embodiment, the treatment time is 150 minutes. In another embodiment, the treatment time is 180 minutes. In another embodiment, the treatment time is 210 minutes. In another embodiment, the treatment time is 240 minutes. The patient can be treated once or multiple times such as twice in one embodiment, or 5, 10, 15, 20, 25, or 30 times in other embodiments of the methods provided herein, in the hyperbaric chamber. Treatment can be administered daily in one embodiment, or every other day, every third day, or weekly in other embodiments. In one embodiment multiple treatments are administered on the same day.

In one embodiment Stromal cell-derived factor-1α (SDF-1α) used in the methods and compositions provided herein is a CXC chemokine with chemoattractant activity for lymphocytes, monocytes, and their progenitor cells. In another embodiment, SDF-1α is an endogenous ligand for the CXC chemokine receptor 4 (CXCR4), binding with the CXCR4 in the form of monomer and the N-terminal eight residues form an important receptor binding patch. In one embodiment, SDF-1α augments production of bone marrow B-cell progenitors in the presence of IL-7.

Figure 15:
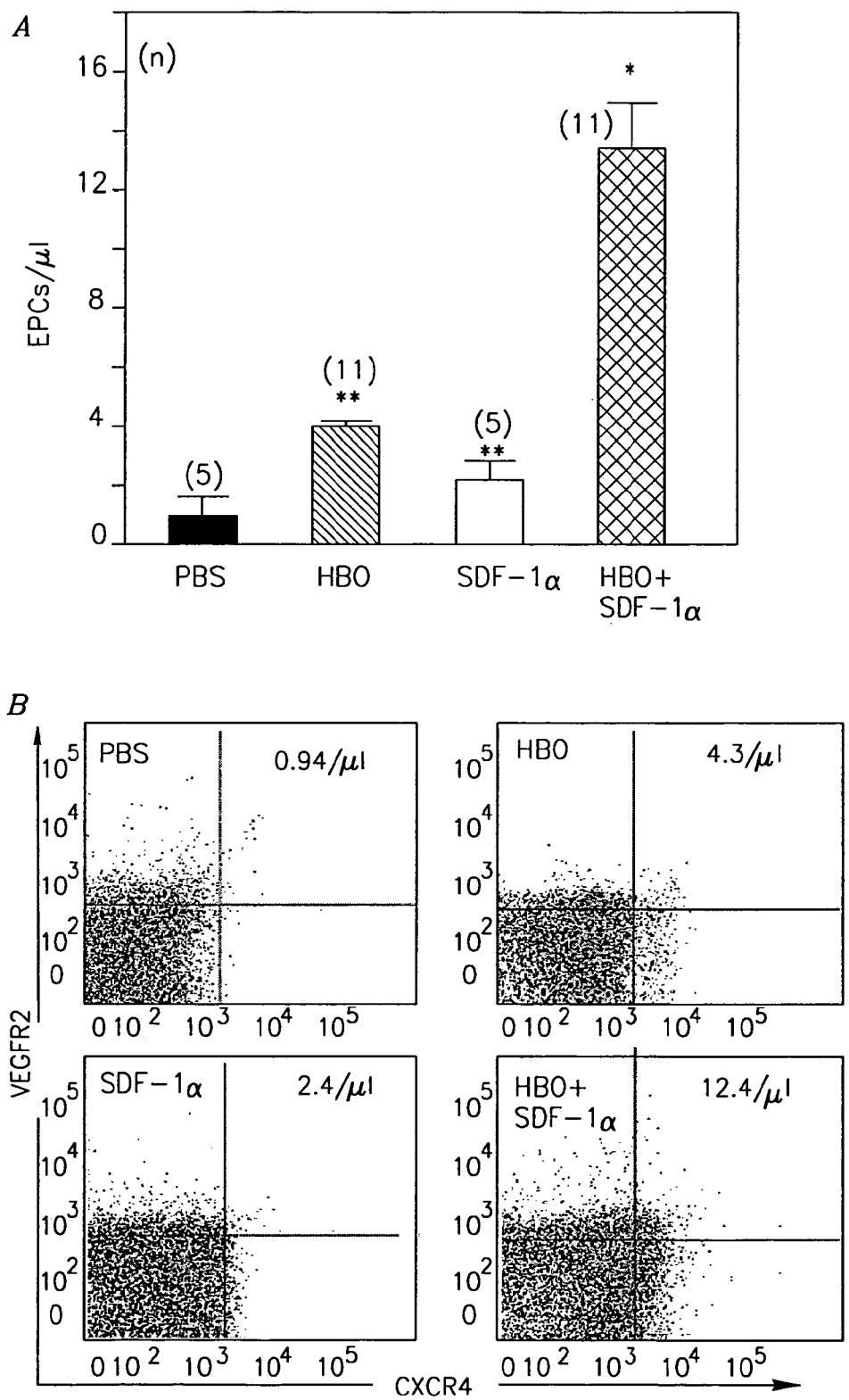
FIG. 15 shows synergistic enhancement of EPC mobilization by HBO and SDF-1α in a murine diabetic model. (A) Diabetic mice were divided into 4 groups that received daily wound injections with either SDF-1α or PBS. Half of the mice also received daily HBO. 48 h post-wounding, peripheral blood was analyzed by flow cytometry. Quantification of EPCs in different groups. Data are based on ten experiments. SDF-1α+HBO treated mice had a significant increase in circuiting EPCs compared to other groups (*P<0.05). SDF-1α and PBS+HBO treated groups demonstrated a statistically significant increase as compared to PBS (**P<0.05). (B) Representative dot plots are shown, with EPC number noted in the CXCR4$^+$/VEGFR2$^+$quadrants. (C) Immunostaining demonstrated a dramatically increased local SDF-1α level in diabetic wound after SDF-1α injection compared to nondiabetic wound. (D) Local administration of SDF-1α causes increased systemic peripheral blood SDF-1α levels. ELISA demonstrated an increased systemic SDF-1α concentration 2 h following wound injection of SDF-1α.
Figure 15:
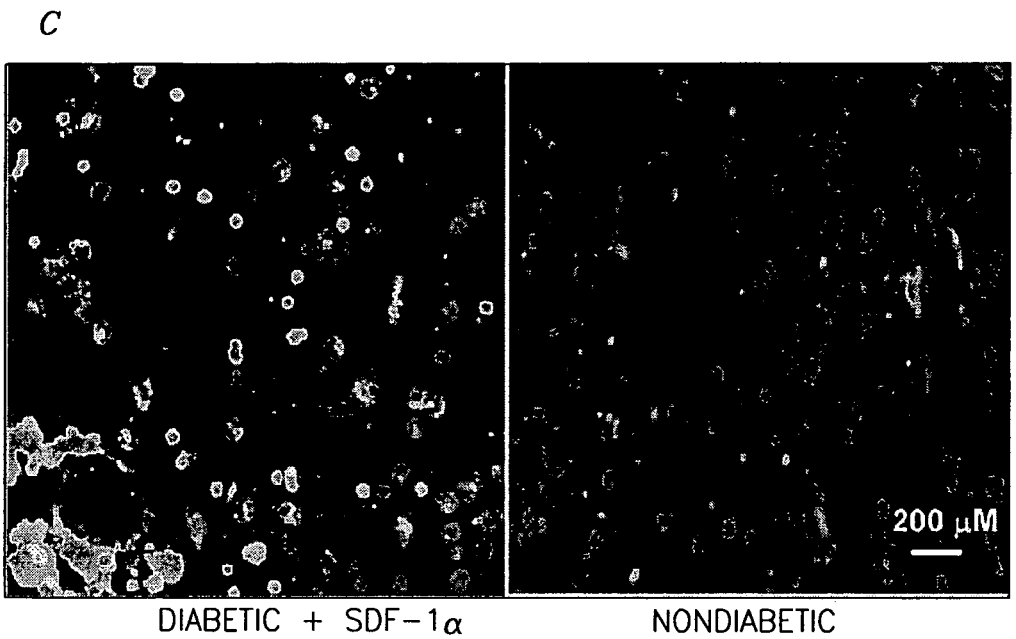
Figure 15:
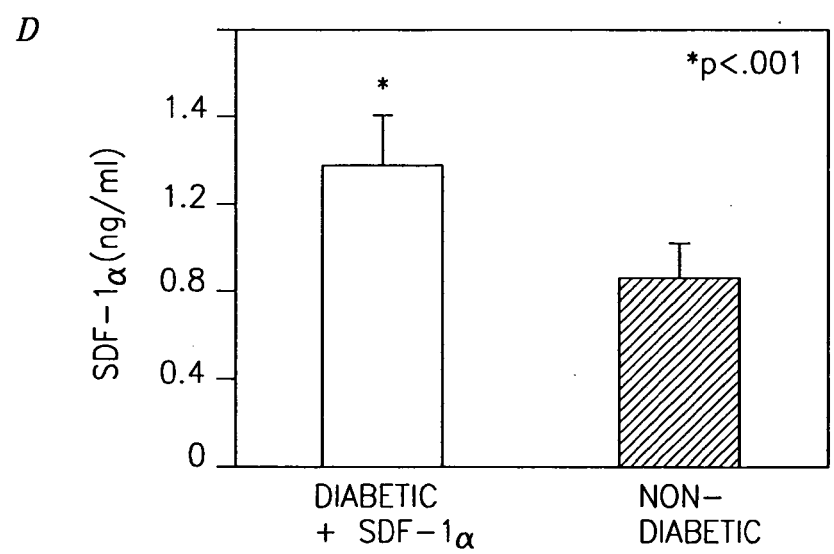

In one embodiment, altering the cytokine milieu of the wound granulation tissue in favor of EPC homing and wound healing leads to broad paracrine effects from factors released by the wound, that at a systemic level, further enhance BM EPC release. In another embodiment, these local factors work in synergism with hyperoxia to greatly increase the systemic mobilization of EPCs. In one embodiment, super-physiological levels of SDF-1α are required for restoring EPC mobilization in diabetic wounds at a much stronger local SDF-1α staining in diabetic (SDF-1α injected) than in nondiabetic wounds (non-SDF-1α injected) (FIG. 15C) and transiently increase systemic peripheral blood SDF-1α levels 2 h after local injection (FIG. 15D). In one embodiment the methods provided herein are carried out between 0 and 3 days post wound formation. In another embodiment, the earlier the co-administration of the homing chemokine and the induction of EPC release into the wound, the faster is the healing of the wound, which in another embodiment, refers to its closing.

In one embodiment, the methods and compositions provided herein for increasing endothelial progenitor cell numbers (EPC) in a wound of a subject, comprise mobilizing endothelial progenitor cells, whereby mobilizing the endothelial progenitor cells comprises exposing the wound to hyperbaric, oxygen-enriched atmosphere, as described herein in another embodiment, thereby increasing endothelial progenitor cells (EPC) release thereby increasing EPC numbers in a wound of a diabetic subject. In another embodiment, the methods and compositions provided herein for increasing endothelial progenitor cell numbers (EPC) in a wound of a subject, comprises homing endothelial progenitor cells into the wound, whereby homing the endothelial progenitor cells into the wound comprises in one embodiment, contacting the wound with a composition comprising an endothelial progenitor cells (EPC) homing chemokine, such as SDF-1α in another embodiment, thereby attracting the endothelial progenitor cells (EPC) to the wound.

In one embodiment, the term "Chemokines" or "chemokine", refers to a superfamily of forty or more small (approximately about 4 to about 14 kDa) inducible and secreted pro-inflammatory cytokines that act primarily as chemoattractants and activators of specific leukocyte cell subtypes. In another embodiment, chemokines target the entire spectrum of leukocyte subtypes; individually each targets only part of the spectrum. In one embodiment, chemokines, which are basic heparin-binding proteins, have four cysteines shared among almost all family members. There are four major groups of to chemokines, three of which include the four conserved cysteines. The groups are defined in one embodiment by the arrangement of the first two cysteines. If the first two cysteines are separated by a single amino acid they are members of the CXC family (also called a); if the cysteines are adjacent, they are classified in the CC family (also called B). If they are separated by three amino acids $CX.sub.3C$, they are members of the third group. The fourth group of chemokines contains two is cysteines, corresponding to the first and third cysteines in the other groups. Structural analysis demonstrates that most chemokines function as monomers and that the two regions necessary for receptor binding reside within the first 35 amino acids of the flexible N-terminus. In one embodiment, any chemokine capable of attracting EPC into the wound is encompassed within the scope of the invention and is considered an embodiment of the invention. In one embodiment, homing chemokine is SDF-1α. In another embodiment, Chemokines, in association with adhesion molecules, recruit subsets of leukocytes to specific sites of inflammation and tissue injury, such as chronic wounds and ulcerations in certain embodiments. In one embodiment, chemokines and chemokine receptor expression are up-regulated in disease, with chemokines acting in an autocrine or paracrine manner. In one embodiment, in subjects exhibiting chronic wound pathologies, no up-regulation of chemokines, or in another embodiment, chemokine receptors occurs, exacerbating the underlying wound aetiology.

In one embodiment, the methods and compositions provided herein, used to accelerate wound healing in a subject in one embodiment, or increase the level of EPC in a wound in another embodiment, further comprise the step of up-regulating the expression of SDF-1α in the subject. In another embodiment, up-regulating comprises contacting the subject with a viral vector carrying a nucleic acid sequence capable of up-regulating the expression of SDF-1α.

A variety of well known vectors can be used to deliver a nucleic acid sequence capable of up-regulating the expression of SDF-1α to cells in a lesion like a diabetic wound in another embodiment, including but not limited to adenoviral vectors and adeno-associated vectors. In another embodiment, naked DNA, liposome delivery methods, or other novel vectors developed to deliver a nucleic acid sequence capable of up-regulating the expression of SDF-1α to cells can also be beneficial. Adenovirus, adeno-associated virus, herpes virus, vacciniavirus, retroviruses, or other viral vectors with the appropriate tropism for cells likely to require enhanced expression of SDF-1α (e.g., keratinocytes and endothelial cells) are used in another embodiment as a transfer delivery system for a nucleic acid sequence capable of up-regulating the expression of SDF-1a. Viral vectors which do not require that the target cell be actively dividing, such as adenoviral and adeno-associated vectors, are used in one embodiment, when the cells are accumulating, but not proliferative. In one embodiment, the vector used to deliver the nucleic acid is a cDNA, carrying a nucleic acid encoding the protein to represented by SEQ ID NO. 1. In another embodiment, SDF-1α is represented by the amino acid sequence represented by SEQ ID NO. 1.

In one embodiment, the nucleic acid sequence capable of up regulating the expression of SDF-1a used in the methods and compositions provided herein, comprises a control region. In another embodiment, "control region" refers to a nucleic acid sequence capable of, required for, assisting or initiating, or otherwise regulating the transcription of a gene, which in one embodiment, encodes the amino acid sequence represented by SEQ ID NO. 1 and include, but is not limited to, promoter, enhancer and other regulatory elements (e.g. those regulating pausing or anti-termination). In one embodimenty, a positive transcription element increases the transcription of a gene encoding SDF-1α. A control region includes in another embodiment a nucleic acid sequence that may or may not be sufficient by itself to initiate, terminate, or otherwise regulate the transcription, yet is able to do so in combination or coordination with other nucleic acid sequences. In one embodiment, a control region can be in nontranscribed regions of a gene, introns or exons. A control region can be in the 5' upstream region or the 3' downstream region to the amino acid coding sequence. A control sequence can be a single regulatory element from a gene. A control region can also have several regulatory elements from a gene linked together. These several regulatory elements can be linked in a way that is substantially the same as in nature or in an artificial way. In one embodiment, the term "nucleic acid" refers to a single stranded or double stranded, DNA or RNA, including those containing modified nucleotides known to one skilled in the art. The complementary strand of an identified sequence is contemplated in another embodiment as well. In one embodiment, the viral vectors used in the methods and compositions provided herein, comprise a control region affecting up regulating the expression of SDF-1α.

In one embodiment, Nitric oxide (NO), is a ubiquitous signaling messenger molecule involved in diverse pathophysiologic processes such as neurotransmission, inflammatory and immune responses, and vascular homeostasis. NO is not stored once produced; and diffuses freely to its site of action where in one embodiment, it binds covalently to its effectors. In one embodiment, hyperoxia activates NOS in the BM, thereby inducing EPC mobilization into circulation by increasing BM NO production. In another embodiment, induction of hyperoxic conditions, causes other NOS isoenzymes to compensate, leading to NO increases in the BM that are substantial.

NO is synthesized in one embodiment by the action of a group of enzymes called NOSs which convert the amino acid L-arginine into NO and another amino acid, L-citrulline. NOSs contain four cofactors: FAD, FMN, tetrahydrobiopterin, and haem; the haem center has spectral properties to resembling those of cytochrome $P_{450}$. There are three types of NOSs. Two are constitutive (named cNOS) and one that is inducible by cytokines and endotoxins (named iNOS). There are two subtypes of cNOS: one in the vascular endothelium named eNOS and the other is present in the central and peripheral nervous systems named nNOS. nNOS and eNOS are $Ca^{2+}$/calmodulin-dependent enzymes. In one embodiment, hyperglycemia inhibits eNOS phosphorylation in bovine arterial ECs, by posttranslational modification at the Akt site. In one embodiment, insulin resistance impairs eNOS activity by increasing endothelial fatty acid oxidation, serving in another embodiment, as a potential mechanism whereby diabetes mellitus results in accelerated atherogenesis and increased cardiovascular disease risk.

In one embodiment, eNOS is essential in the BM microenvironment and in another embodiment, an increases in marrow NO levels results in the mobilization of EPCs from BM niches to circulation, ultimately allowing for their participation in tissue-level vasculogenesis and wound healing according to the methods provided herein. In another embodiment, $HBO_2$ stimulates EPC mobilization by a •NO dependent mechanism. In another embodiment the sequence of events is as follows: $HBO_2 \rightarrow NOS \rightarrow •NO \rightarrow$ nitrosylation of $MMP9 \rightarrow$ cleavage of membrane-bound $SCF \rightarrow SCF$ prompts EPC proliferation and mobilization$\rightarrow$EPC released into peripheral circulation. A person skilled in the art would readily recognize that any compound now known, or later discovered or developed, which would perform the functions in the cascade described hereinabove and result in EPC released into peripheral circulation, is encompassed by the present invention.

In one embodiment, the methods of increasing the level of EPC in a wound, or the compositions therefore, are useful wherein the wound is a livedoid vasculopathy. In another embodiment, the wound is a diabetic ulcer. In another embodiment, the wound is a peripheral arterial disease ulcer. In another embodiment, the wound is a venous stasis ulcer. In another embodiment, the wound is a chronic non-healing ulcer. In another embodiment, the wound is a pressure ulcer, or in another embodiment, the wound is a combination thereof.

In one embodiment, the term "livedoid vasculopathy" refers to a disorder characterised by painful ulceration in association with livedo reticularis and atrophie blanche. In another embodiment, Livedoid vasculopathy (LV) is an occlusive thrombotic disease that affects primarily the small blood vessels of the lower extremities is associated in another embodiment with recurrent painful ulcerations. The pathogenesis of LV is attributed in one embodiment, to a hypercoagulable state. Factor V Leiden mutation, heterozygous protein C deficiency, homozygous hyperhomocysteinemia, and other inherited thrombophilias have been associated in other embodiments with LV. In one embodiment, provided herein is a method of accelerating the healing of ulcerations due to livedoid vasculopathy, comprising mobilizing endothelial progenitor cells using HBO therapy of no less than 5 daily treatments; and using direct injection into the ulceration; simultaneously homing the endothelial progenitor cells into the ulcerations due to livedoid vasculopathy, thereby increasing EPC numbers in an ulcerations due to livedoid vasculopathy.

In another embodiment, the methods and compositions provided herein, are useful in treating dermal ulcerations. Dermal ulcers refer in one embodiment to lesions on the skin caused by superficial loss of tissue that fail to heal normally due to defects in healing processes, vascular insufficiency or pressure. Dermal skin ulcers which can be treated by the methods and compositions provided herein are decubitus ulcers, diabetic ulcers, venous stasis ulcers and arterial ulcers. Decubitus wounds refer to chronic ulcers that result from pressure applied to areas of the skin for extended periods of time. In another embodiment, wounds of this type are called bedsores or pressure sores. Venous stasis ulcers result from the stagnation of blood or other fluids from defective veins. Arterial ulcers refer to necrotic skin in the area around arteries having poor blood flow. In one embodiment, recruitment of EPC into the lesions will accelerate the healing of these wounds.

In one embodiment, provided herein is a method of increasing endothelial progenitor cell numbers (EPC) in a wound of a subject, comprising: mobilizing endothelial progenitor cells; and homing the endothelial progenitor cells into the wound, thereby increasing EPC numbers in a wound of the subject, whereby mobilizing the endothelial progenitor cells comprises exposing the wound to hyperbaric, oxygen-enriched atmosphere, thereby increasing endothelial progenitor cells (EPC) release; and whereby homing the endothelial progenitor cells into the wound comprises contacting the wound with a composition comprising an endothelial progenitor cells (EPC) homing chemokine, thereby attracting the endothelial progenitor cells (EPC) to the wound. In one embodiment, contacting the wound with a composition comprising an endothelial progenitor cells (EPC) homing chemokine is via topical irrigation. In another embodiment, contacting the wound with a composition comprising an endothelial progenitor cells (EPC) homing chemokine is via parenteral administration. In another embodiment, contacting the wound with a composition comprising an endothelial progenitor cells (EPC) homing chemokine is via oral administration. In another embodiment, contacting the wound with a composition comprising an endothelial progenitor cells (EPC) homing chemokine is via intramuscular administration. In another embodiment, contacting the wound with a composition comprising an endothelial progenitor cells (EPC) homing chemokine is via subcutaneous administration. In another embodiment, contacting the wound with a composition comprising an to endothelial progenitor cells (EPC) homing chemokine is via a foam. In another embodiment, contacting the wound with a composition comprising an endothelial progenitor cells (EPC) homing chemokine is via a patch administration. In another embodiment, contacting the wound with a composition comprising an endothelial progenitor cells (EPC) homing chemokine is via a local wound injection. In another embodiment, contacting the wound with a composition comprising an endothelial is progenitor cells (EPC) homing chemokine is via an ointment. In another embodiment, contacting the wound with a composition comprising an endothelial progenitor cells (EPC) homing chemokine is via a cream, or their combination in other embodiments.

In another embodiment, the methods and compositions provided herein are useful in treating subjects who are diabetic. In another embodiment, in the setting of diabetes, hyperoxia increases BM NO level and stimulates EPC release from the BM into circulation, without significantly impacting the inflammatory cell numbers in circulation. In another embodiment a synergistic increase in EPC mobilization, homing, and wound healing is achieved when used in conjunction with HBO. In another embodiment, HBO-mediated EPC release by NOS activation, SDF-1α-mediated EPC homing and their combination, as well as timing the initiation of such a therapy to the initial stages of the diabetic wound carry important clinical weight in diabetic wound healing.

In one embodiment, provided herein is a method of accelerating a wound healing in a subject, comprising increasing release of endothelial progenitor cells from a bone marrow of said subject, and attracting the endothelial progenitor cells into the wound, thereby accelerating a wound healing in the subject. In another embodiment, the subject is diabetic.

In one embodiment, the compositions provided herein, are used in the methods provided herein. Accordingly and in one embodiment, provided herein is a composition for accelerating a wound healing in a subject, comprising an endothelial progenitor cells (EPC) homing chemokine, its isomer, its metabolite, or a salt thereof, wherein said endothelial progenitor cells (EPC) homing chemokine attract endothelial progenitor cells into the wound, thereby accelerating wound healing. In one embodiment, the endothelial progenitor cells (EPC) homing chemokine used in the compositions provided herein, is SDF-1α.

In another embodiment, the composition for accelerating a wound healing in a subject, comprising an endothelial progenitor cells (EPC) homing chemokine, its isomer, its metabolite, or a salt thereof, further comprise an agent capable of upregulating expression of SDF-1α. In another embodiment, the agent capable of upregulating expression of SDF-1α is a viral vector carrying a nucleic acid sequence capable of upregulating the expression of SDF-1α. The embodiments of compositions vectors and the like, described hereinabove are used in one embodiment in the compositions described herein.

In one embodiment, the composition for accelerating a wound healing in a subject, comprising an endothelial progenitor cells (EPC) homing chemokine, its isomer, its metabolite, or a salt thereof, further comprise a carrier, an excipient, a lubricant, a flow aid, a processing aid or a diluent, wherein said carrier, excipient, lubricant, flow aid, processing aid or diluent is a gum, a starch, a sugar, a cellulosic material, an acrylate, calcium carbonate, magnesium oxide, talc, lactose monohydrate, magnesium stearate, colloidal silicone dioxide or mixtures thereof.

In one embodiment, the composition further comprises a carrier, excipient, lubricant, flow aid, processing aid or diluent, wherein said carrier, excipient, lubricant, flow aid, processing aid or diluent is a gum, starch, a sugar, a cellulosic material, an acrylate, calcium carbonate, magnesium oxide, talc, lactose monohydrate, magnesium stearate, colloidal silicone dioxide or mixtures thereof.

In another embodiment, the composition further comprises a binder, a disintegrant, a buffer, a protease inhibitor, a surfactant, a solubilizing agent, a plasticizer, an emulsifier, a stabilizing agent, a viscosity increasing agent, a sweetner, a film forming agent, or any combination thereof.

In one embodiment, the composition for accelerating a wound healing in a subject, comprising an endothelial progenitor cells (EPC) homing chemokine, its isomer, its metabolite, or a salt thereof, that are described herein and may be present in the form of suspension or dispersion form in solvents or fats, in the form of a nonionic vesicle dispersion or else in the form of an emulsion, preferably an oil-in-water emulsion, such as a cream or milk, or in the form of an ointment, gel, cream gel, sun oil, solid stick, powder, aerosol, foam or spray.

In one embodiment, the composition is a particulate composition coated with a polymer (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermally, subcutaneously, intraperitonealy, to intraventricularly, or intracranially.

In some embodiments, the compositions and methods provided herein permit direct application to the site where it is needed. In the practice of the methods provided herein, it is contemplated that virtually any of the compositions provided herein can be employed.

In one embodiment, the compositions of this invention may be in the form of a pellet, a tablet, a capsule, a solution, a suspension, a dispersion, an emulsion, an elixir, a gel, an ointment, a cream, or a suppository.

In another embodiment, the composition is in a form suitable for oral, intravenous, intraarterial, intramuscular, subcutaneous, parenteral, transmucosal, transdermal, or topical administration. In one embodiment the composition is a controlled release composition. In another embodiment, the composition is an immediate release composition. In one embodiment, the composition is a liquid dosage form. In another embodiment, the composition is a solid dosage form.

In another embodiment, the compositions provided herein are suitable for oral, intraoral, rectal, parenteral, topical, epicutaneous, transdermal, subcutaneous, intramuscular, intranasal, sublingual, buccal, intradural, intraocular, intrarespiratory, nasal inhalation or a combination thereof. In one embodiment, the step of administering the compositions provided herein, in the methods provided herein is carried out as oral administration, or in another embodiment, the administration of the compositions provided herein is intraoral, or in another embodiment, the administration of the compositions provided herein is rectal, or in another embodiment, the administration of the compositions provided herein is parenteral, or in another embodiment, the administration of the compositions provided herein is topical, or in another embodiment, the administration of the compositions provided herein is epicutaneous, or in another embodiment, the administration of the compositions provided herein is transdermal, or in another embodiment, the administration of the compositions provided herein is subcutaneous, or in another embodiment, the administration of the compositions provided herein is intramuscular, or in another embodiment, the administration of the compositions provided herein is intranasal, or in another embodiment, the administration of the compositions provided herein is sublingual, or in another embodiment, the administration of the compositions provided herein is buccal, or in another embodiment, the administration of the compositions provided herein is intradural, or in another embodiment, the administration of the compositions provided herein is intraocular, or in another embodiment, the administration of the compositions provided herein is intrarespiratory, or in another embodiment, the administration of the compositions provided herein is nasal inhalation or in another embodiment, the administration of the compositions provided herein is a combination thereof.

In one embodiment, the method of the invention comprises administering a the compositions provided herein via an intradermal patch. The method in some embodiments also comprises administering the patch adjacent to the area of skin to be treated. As used herein a "patch" comprises at least the compositions provided herein and a covering layer, such that, the patch can be placed over the area of skin to be treated. In another embodiment, the patch is designed to maximize delivery of the compositions provided herein through the stratum corneum and into the epidermis or dermis, reduce lag time, promote uniform absorption, and reduce mechanical rub-off.

In some embodiments, the method comprises administering a topical formulation of the compositions provided herein to an affected site of skin. In some embodiments, topical administration according to the present invention comprises aerosol, cream, foam, gel, liquid, ointment, paste, powder, shampoo, spray, patch, disk, or dressing.

The compounds utilized in the methods and compositions of the present invention may be present in the form of free bases in one embodiment or pharmaceutically acceptable acid addition salts thereof in another embodiment. In one embodiment, the term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I are prepared in another embodiment, from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, b-hydroxybutyric, salicylic, galactaric and galacturonic acid. Suitable pharmaceutically-acceptable base addition salts include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound by reacting, in another embodiment, the appropriate acid or base with the compound.

In one embodiment, the term "pharmaceutically acceptable carriers" includes, but is not limited to, may refer to 0.01-0.1M and preferably 0.05M phosphate buffer, or in another embodiment 0.8% saline. Additionally, such pharmaceutically acceptable carriers may be in another embodiment aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. In one embodiment the level of phosphate buffer used as a pharmaceutically acceptable carrier is between about 0.01 to about 0.1M, or between about 0.01 to about 0.09M in another embodiment, or between about 0.01 to about 0.08M in another embodiment, or between about 0.01 to about 0.07M in another embodiment, or between about 0.01 to about 0.06M in another embodiment, or between about 0.01 to about 0.05M in another embodiment, or between about 0.01 to about 0.04M in another embodiment, or between about 0.01 to about 0.03M in another embodiment, or between about 0.01 to about 0.02M in another embodiment, or between about 0.01 to about 0.015 in another embodiment.

In one embodiment, the compounds of this invention may include compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The pharmaceutical preparations comprising the compositions used in one embodiment in the methods provided herein, can be prepared by known dissolving, mixing, granulating, or tablet-forming to processes. For oral administration, the active ingredients, or their physiologically tolerated derivatives in another embodiment, such as salts, esters, N-oxides, and the like are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. Examples of suitable inert vehicles are conventional tablet bases such as lactose, sucrose, or cornstarch in combination with binders such as acacia, cornstarch, gelatin, with disintegrating agents such as cornstarch, potato starch, alginic acid, or with a lubricant such as stearic acid or magnesium stearate.

Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the active ingredients or their physiologically tolerated derivatives such as salts, esters, N-oxides, and the like are converted into a solution, suspension, or emulsion, if desired with the substances customary and suitable for this purpose, for example, solubilizers or other auxiliaries. Examples are sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

In addition, the composition described in the embodiments provided herein, can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In one embodiment, the compositions described herein, which are used in another embodiment, in the methods provided herein, further comprise a carrier, an excipient, a lubricant, a flow aid, a processing aid or a diluent.

The active agent is administered in another embodiment, in a therapeutically effective amount. The actual amount administered, and the rate and time-course of administration, will depend in one embodiment, on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences*.

Alternatively, targeting therapies may be used in another embodiment, to deliver the active agent more specifically to certain types of cell, by the use of targeting systems such as antibodies or cell specific ligands. Targeting may be desirable in one embodiment, for a variety of reasons, e.g. if the agent is unacceptably toxic, or if it would otherwise require too high a dosage, or if it would not otherwise be able to enter the target cells.

The compositions of the present invention are formulated in one embodiment for oral delivery, wherein the active compounds may be incorporated with excipients and used in the form of ingestible tablets, buccal tables, troches, capsules, elixirs, suspensions, syrups, wafers, and the like. The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar, or both. Syrup of elixir may contain the active compound sucrose as a sweetening agent methyl and propylparabens as preservatives, a dye and flavoring, such as cherry or orange flavor. In addition, the active compounds may be incorporated into sustained-release, pulsed release, controlled release or postponed release preparations and formulations.

Controlled or sustained release compositions include formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

In one embodiment, the composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In another embodiment, a controlled release system can be placed in proximity to the therapeutic target, i.e., the brain, thus requiring only a fraction of the systemic dose (see, e.g., Goodson, in Medical Applications of Controlled Release, supra, vol. 2, pp. 115-138 (1984). Other controlled release systems are discussed in the review by Langer (Science 249:1527-1533 (1990).

Such compositions are in one embodiment liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc., or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms, protective coatings, protease inhibitors, or permeation enhancers for various routes of administration, including parenteral, pulmonary, nasal, and oral.

In another embodiment, the compositions of this invention comprise one or more, pharmaceutically acceptable carrier materials.

In one embodiment, the carriers for use within such compositions are biocompatible, and in another embodiment, biodegradable. In other embodiments, the formulation may provide a relatively constant level of release of one active component. In other embodiments, however, a more rapid rate of release immediately upon administration may be desired. In other embodiments, release of active compounds may be event-triggered. The events triggering the release of the active compounds may be the same in one embodiment, or different in another embodiment. Events triggering the release of the active components may be exposure to moisture in one embodiment, lower pH in another embodiment, or temperature threshold in another embodiment. The formulation of such compositions is well within the level of ordinary skill in the art using known techniques. Illustrative carriers useful in this regard include microparticles of poly(lactide-co-glycolide), polyacrylate, latex, starch, cellulose, dextran and the like. Other illustrative postponed-release carriers include supramolecular biovectors, which comprise a non-liquid hydrophilic core (e.g., a cross-linked polysaccharide or oligosaccharide) and, optionally, an external layer comprising an amphiphilic compound, such as phospholipids. The amount of active compound contained in one embodiment, within a sustained release formulation depends upon the site of administration, the rate and expected duration of release and the nature of the condition to be treated suppressed or inhibited.

In another embodiment, the composition for accelerating a wound healing in a subject, comprising an endothelial progenitor cells (EPC) homing chemokine, its isomer, its metabolite, or a salt thereof, further comprise one or more additional agent for treating a wound in the subject. In one embodiment, the one or more additional agent for treating a wound in the subject is mesenchymal stem cells (MSC). In another embodiment, the one or more additional agent for treating a wound in the subject is phenyloin. In another embodiment, the one or more additional agent for treating a wound in the subject is autologous keratinocytes in fibrin sealant (Bioseed-S™). In another embodiment, the one or more additional agent for treating a wound in the subject is dalteparin, or in another embodiment, the one or more additional agent for treating a wound in the subject is a combination thereof.

In one embodiment, the wound for which healing is sought to be accelerated, require the grafting of skin tissue on the lesion. In another embodiment, mesenchymal stem cells are used to condition a recipient's immune system to donor or foreign tissue by administering to the recipient, prior to, or at the same time as transplantation of the donor tissue, mesenchymal stem cells in an amount effective to reduce or eliminate an immune response against the transplant by, for example, the recipient's T cells. In another embodiment, provided herein is a method of accelerating a burn wound healing in a subject requiring skin graft, comprising increasing release of endothelial progenitor cells from a bone marrow of said subject, and attracting the endothelial progenitor cells into the burn wound, and further comprising one or more additional agent for treating the burn wound in the subject, wherein the one or more additional agent for treating a wound in the subject is mesenchymal stem cells (MSC), conditioning the subject's immune system to donor or foreign skin graft, thereby accelerating a wound healing in the subject. In another embodiment, mobilizing and attracting is done according to the description provided herein.

In one embodiment, phenyloin is involved in the healing process at several levels including stimulating fibroblast proliferation in one embodiment, or enhancing the formation of granulation tissue, decreasing collagenase activity (by reducing its production or secretion or both), promoting deposition of collagen and other connective tissue components, decreasing bacterial contamination, and decreasing wound exudate or their combination in other embodiments. In another embodiment, biopsies of phenyloin-treated open wounds show neovascularization, collagenization, and decreased polymorphonuclear and eosinophil cell infiltration. In one embodiment, provided herein is a method of accelerating healing of a decubitus ulcer in a subject, comprising increasing release of endothelial progenitor cells from a bone marrow of said subject, and attracting the endothelial progenitor cells into the decubitus ulcer; and further comprising one or more additional agent for treating decubitus ulcers in the subject, wherein the one or more additional agent for treating decubitus ulcers in the subject is phenyloin cream topically onto the ulcerations promoting deposition of collagen and other connective tissue components, thereby accelerating decubitus ulcers healing in the subject.

In one embodiment, autologous keratinocytes in fibrin sealant are used following treatment of wounds as described herein. In one embodiment, the term "autologous" as applied to components of compositions administered to recipients refers to body components (e.g., cells or biological molecules such as proteins, nucleic acids, carbohydrates or lipids) removed from a donor and administered to a recipient, wherein the donor and recipient are the same individual. Accordingly and in another embodiment, provided herein is a method of accelerating healing of pressure wound, comprising increasing release of endothelial progenitor cells from a bone marrow of said subject, and attracting the endothelial progenitor cells into the pressure wound; and further comprising one or more additional agent for treating pressure wound in the subject, wherein the one or more additional agent for treating pressure wound in the subject is an aerosolized autologous keratinocytes suspended in fibrin sealant, sprayed on wound after treatment according to the methods provided herein, thereby providing keratinocytes to the wound site and accelerating its healing.

Chronic foot ulcers are a common, severe, and expensive complication threatening life and limb in patients with diabetes. In one embodiment, provided herein is a method of accelerating healing of foot ulcers secondary to diabetes or ischemia in a subject, comprising increasing release of endothelial progenitor cells from a bone marrow of said subject, and attracting the endothelial progenitor cells into the foot ulcers secondary to diabetes or ischemia, and further comprising one or more additional agent for treating the foot ulcers secondary to diabetes or ischemia in the subject, wherein the one or more additional agent for treating foot ulcers secondary to diabetes or ischemia in the subject is a subcutaneously injected dalteparin into the wound, improving local capillary circulation, thereby accelerating healing of foot ulcers secondary to diabetes or ischemia in the subject.

In one embodiment, provided herein is a method of accelerating wound healing in a subject, comprising the step of increasing eNOS expression or function thereby increasing endothelial progenitor cells (EPC) release from bone marrow. In another embodiment, increasing eNOS expression or function comprises perfusion of autologous BM with NO ex-vivo and reincorporating the perfused BM cells into the subject. In another embodiment, viral vectors as described hereinabove are used to increase the expression of nucleic acids encoding for eNOS. In another embodiment, the step of increasing eNOS expression or function, comprises contacting the subject with a composition that upregulates eNOS. In another embodiment the step of increasing eNOS expression or function, comprises contacting the subject with a composition that activates eNOS. In another embodiment the step of increasing eNOS expression or function, comprises contacting the subject with a composition that induces phosphorylation of eNOS or in another embodiment the step of increasing eNOS expression or function, is a combination thereof, thereby increasing endothelial progenitor cells (EPC) release from bone marrow. In one embodiment, the invention encompasses the use of a compound that upregulates or activates SDF-1α, for accelerating wound healing in a subject. In another embodiment, the invention encompasses the use of a compound that upregulates or activates SDF-1α, for accelerating wound healing in a diabetic subject.

Therapeutic interventions such as those described in the methods provided herein, comprising the correction of both EPC activation via HBO in one embodiment, and EPC homing via administration of SDF-1α in another embodiment, significantly accelerate diabetic wound healing by correcting the EPC deficit inherent to diabetic wounds.

The term "about" as used herein means in quantitative terms plus or minus 5%, or in another embodiment plus or minus 10%, or in another embodiment plus or minus 15%, or in another embodiment plus or minus 20%.

The term "subject" refers in one embodiment to a mammal including a human in need of therapy for, or susceptible to, a condition or its sequalae. The subject may include dogs, cats, pigs, cows, sheep, goats, horses, rats, and mice and humans. The term "subject" does not exclude an individual that is normal in all respects.

The following examples are presented in order to more fully illustrate the preferred embodiments of the invention. They should in no way be construed, however, as limiting the broad scope of the invention.

EXAMPLES

Materials and Methods

Mice

All procedures were done with approval from the University of Pennsylvania Institutional Animal Care and Use Committee (IACUC). 6-12 wk-old FVB wild-type mice (FVB/NJ), GFP (FVB/Tg) and Tie2-GFP (Tg(TIE2GFP)87 Sato/J) were purchased from The Jackson Laboratory. For all surgical procedures, mice were anesthetized with an i.p. injection of 80 mg/kg of ketamine (Phoenix Scientific, Inc.) and 20 mg/kg xylazine (Vedco Inc.). For BM transplantation experiments, $1\times10^7$ BM cells from GFP mice were transplanted to γ-irradiated (900 Rad) FVB wild type mouse via tail vein. Reconstitution of BM system in chimeras was achieved in 3 wk and confirmed by FACScan (>50% BM cells are GFP$^+$, data not shown). For local wound SDF-1α injection, SDF-1α protein (R&D Systems) was reconstituted in PBS and injected into the wound base (25 μg/Kg).

Induction of Diabetes and Generation of Peripheral Wounds

Tie2-GFP, wild-type or chimeric FVB mice at 6-12 wk of age were treated with STZ (Sigma-Aldrich) to induce diabetes. Mice were rendered diabetic by i.p. administration of 60 mg/kg STZ in 50 mM sodium citrate, pH 4.5, daily for 5 d. Control mice were treated with daily injections of citrate buffer. Serum glucose was measured from the mouse tail vein using a glucometer. Once serum glucose reached 250 mg/dL, mice were followed with daily measurements for 1 wk prior to use in experiments. Serum glucose levels in STZ mice averaged 461 mg/dL with a range of 372-520 mg/dL, while control mice serum glucose mean level was 120 mg/dL with a range of 94-135 mg/dL. Wounds were induced on the ventral surface of the mouse thigh using a 4 mm punch biopsy. Full-thickness skin was removed, exposing the underlying muscle.

HBO Treatment and In Vivo BM NO Measurements

For HBO treatment, mice were placed in an animal hyperbaric chamber (Reneau Corp.) and subjected to 100% oxygen at 2.4 atmospheres absolute (ATA) for 90 min (Davis Wound Healing Protocol). To measure continuous, real-time BM NO levels, NO microelectrodes was inserted into the femoral marrow cavity as previously described. An osteotomy was created on the patellar surface of the murine femur using a 25 G beveled needle, allowing the electrode to be lowered into the marrow space when the animal was placed in the hyperbaric chamber. In some mice, pretreatment with L-NAME (40 mg/kg i.p.) (Sigma-Aldrich) was given 2 h prior to exposure to HBO.

Western Blot Analysis

Isolation of whole BM from FVB/NJ mice (n=12/group) was obtained by flushing harvested femurs and tibias with PBS/2% FBS. Red blood cells were removed by Red Cell Lysis Buffer (Sigma-Aldrich). Isolated BM cells were then lysed and protein concentrations were determined by DC protein assay (Bio-Rad Laboratories). Equal amounts of protein were subjected to 4-12% SDS gel electrophoresis under reducing conditions. The transferred PVDF membranes were probed with primary Ab (anti-eNOS and anti-phospho-eNOS (Ser$^{1177}$) (BD Biosciences) diluted 1:500 in 1% milk in TBST buffer and then incubated with HRP-conjugated second Ab (DakoCytomation Inc.). Proteins were visualized using enhanced chemiluminescence (Amersham Bioscience).

Real-Time RT-PCR

Total RNA was isolated from wound tissues by Trizol (Invitrogen) in tissue grinders. cDNA was synthesized from 500 ng of total RNA using TaqMan Gold RT-PCR Kit (Applied Biosystems) according to manufacturer's protocol. The cDNA samples were diluted 20-fold, real-time PCR reaction was carried out using SYBR green JumpStart™ Taq Ready-Mix™ (Sigma-Aldrich) with 100 μM of primer. Amplifications were performed in an ABI PRISM 7000 Sequence Detection System™ (Applied Biosystems). Thermal cycler conditions were 50° C. for 2 min and 95° C. for 10 min to activate/inactivate different enzymes, then 40 cycles of 15 sec at 95° C. (denaturation) followed by 1 min at 59° C. (annealing and extension). The β-actin plasmid was used as standard DNA. All standards and samples were assayed in triplicate. The threshold cycle (Ct) values were used to plot a standard curve. All samples were normalized to the relative levels of β-actin (setting as "1"), and results expressed as fold-increase in relative levels. Primers were designed using PrimerExpress™ (Applied Biosystems) software as follows: SDF-1α: 5'-CCAGAGCCAACGTCAAGCAT-3' (SEQ ID NO. 1) and 5'-TGTTGAGGATTTTCAGATGCTTGA-3'(SEQ ID NO. 1); and /actin: 5'-ACGGCCAGGTCATCACTATTG-3' (SEQ ID NO. 2) and 5'-CAA GAA GGA AGG CTG GAA AAG A-3' (SEQ ID NO. 3).

ELISA

Mouse serum SDF-1α concentration was measured by Quantikine® mouse SDF-1α ELISA kit (R&D Systems) based on manufacturer's protocol.

Multicolor Flow Cytometry

Mobilization of EPCs into circulation was studied using flow cytometry as previously described. Cells isolated from mice were incubated with various Abs (BD Biosciences). Isotype matched mouse immunoglobulins served as controls. One million viable cells were analyzed per sample using an LSR2 multicolor flow cytometer (BD Biosciences). Data was analyzed using FlowJo software (Treestar, Inc.).

Histochemistry

For immunostaining, paraffin embedded serial sections (5 μm) were first underwent standard deparaffinizing and rehydration procedures and then probed with various Abs. To assess wound SDF-1α$^+$ cells, sections were double-stained with HTC-conjugated anti-SDF-1α and PE-conjugated different tissue-specific Abs (eBiosciences). To detect blood vessels in wound, sections were stained with HTC-conjugated anti-VEGFR2Ab. For examination of wound EPC recruitment in BM transplantation experiment, sections were double-stained with FITC-GFP and PE-VEGFR2 (BD Biosciences). Nuclei were counterstained with Hoescht dye. Masson's trichrome staining and H&E staining were performed using standard method and all reagents were from Sigma-Aldrich. Tissue sections were analyzed using fluorescence microscopy and ImageJ (NIH) software to quantitate fluorescent intensity. In trichrome stained slides, blue stain (collagen content) was also quantitatively analyzed by ImageJ.

Assessment of Peripheral Wound Healing

Initial wound surface area was recorded and wounds were then followed serially with daily digital photographs using an Olympus digital camera. Photographs contained an internal scale to allow for standard calibration of measurements. Wound area was quantified using ImageJ software. Wound area was expressed as the percentage of original wound size. Wounds were followed for 6 d and mice were sacrificed at the conclusion of the experiment.

Statistical Analysis

All data is expressed as mean±SEM. Statistical analysis carried out using paired Student's t-test and analysis of variance (ANOVA) procedures. Values considered statistically significant were P<0.05.

Example 1

HBO$_2$ Increases Circulating EPC in Humans

Figure 2:
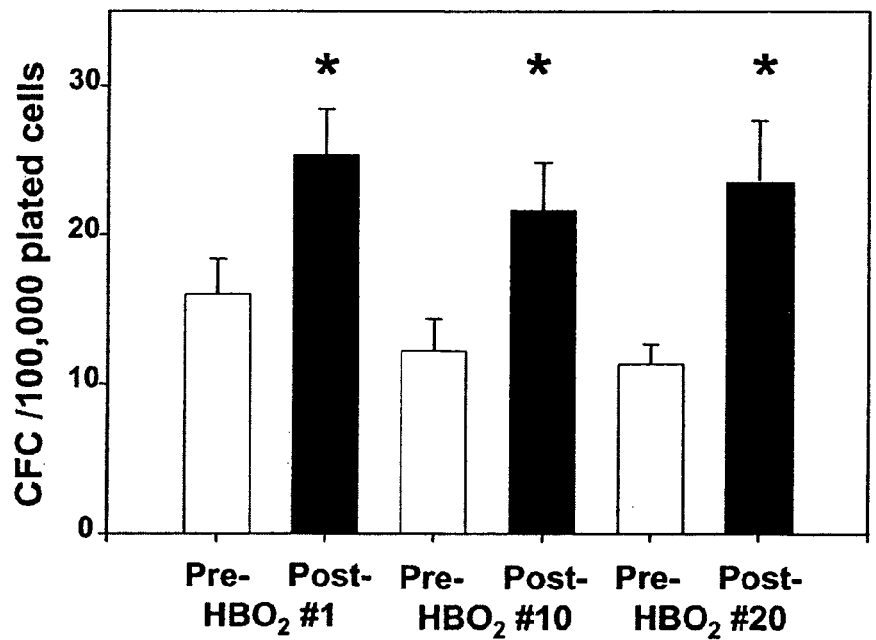
FIG. 2 shows colony forming cells in blood of humans before and after $HBO_2$ treatments. Data are the colonies counted after a 14 day incubation. *t-test performed on each data set pre/post-1$^{st}$ treatment, p=0.036; pre/post-10$^{th}$ treatment, p=0.041; pre/post-20$^{th}$ treatment, p=0.049.

In initial human studies on the mobilization of EPC by HBO$_2$, blood was obtained from 26 patients before and after their first, 10$^{th}$ and 20$^{th}$ hyperbaric treatment for osteoradionecrosis prophylaxis (the standard pre-operative course of therapy is 20 treatments). Blood leukocytes were harvested and analyzed for the presence of EPC based on flow cytometry and colony forming cells (CFCs). Control human subjects included patients breathing 100% O$_2$ but not pressurized and pressurized attendants not breathing 100% O$_2$ where tissue level hyperoxia is not achieved. In HBO$_2$-treated patients (but not controls), the CD34+ population in blood (FIG. 1) and the number of colony forming cells (CFCs) in peripheral blood were significantly increased in response to each exposure to HBO$_2$ (FIG. 2). Of note, elevations in CFCs prior to the 10$^{th}$ and 20$^{th}$ treatments (FIG. 2) were not found, although the numbers of CD34+ cells were elevated (FIG. 1). This suggested that only cells recently mobilized by HBO$_2$ exhibit an increased propensity to grow and form colonies, a subject that is currently being actively investigated in our laboratory.

Figure 3:
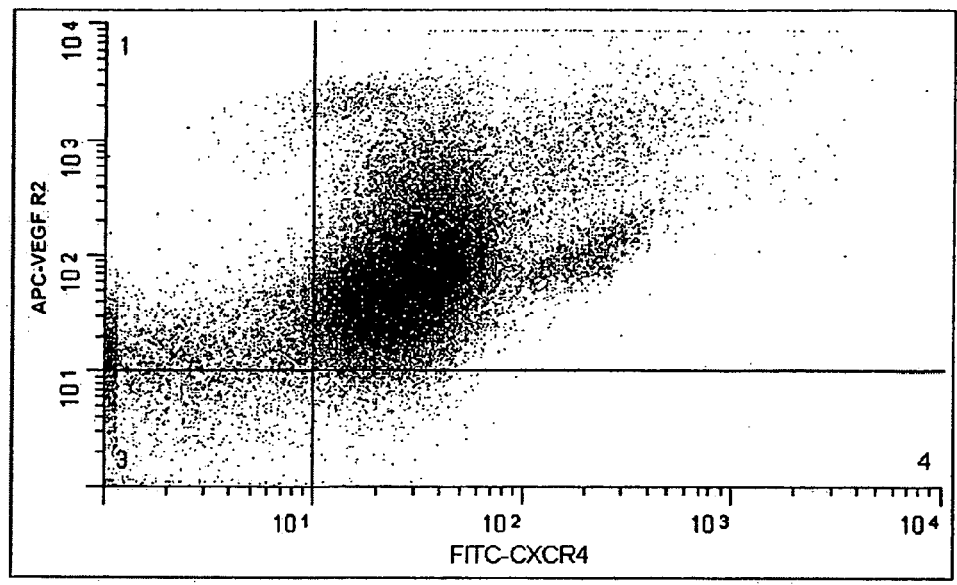
FIG. 3 shows expression of surface markers on progeny of mobilized CD34+ cells. Figure shows results from 50,000 cells.

To specifically address whether the increased CFCs were coming from the fraction of cells expressing CD34, the circulating monocyte population of 9 patients before and after their 20$^{th}$ HBO$_2$ treatment were isolated and fractionated using paramagnetic polystyrene beads coated with antibody to CD34. In the CD34$^+$ fraction, prior to treatment there were 13±0.3 colonies, and after HBO$_2$ 23±3 colonies grew (p<0.05); whereas in the CD34$^-$ fraction, 12±0.7 colonies grew prior to treatment and 13±0.6 (NS) grew after HBO$_2$. This data indicated that the CD34$^+$ cell fraction (that contains the EPC pool) were the ones that exhibited improved growth potential in response to hyperoxia. Characterizing these cell surface antigenic phenotype of the cell colonies was also of interest. Colonies were harvested, washed, and stained with antibodies. FIG. 3 shows a typical flow cytometry scatter plot demonstrating that a large number of these cells express CXCR4 and VEGFR-2, which are highly specific markers for EPC. As CXCR4 is required for EPC homing to sites of injury/ischemia, and both CXCR4 and VEGFR-2 are co-expressed on endothelial progenitor cells, these findings indicate that the cells mobilized by HBO$_2$ are EPC and may be functional in improving neovascularization.

Example 2

HBO$_2$ Increases Circulating EPC in Mice Via NOS

Figure 4:
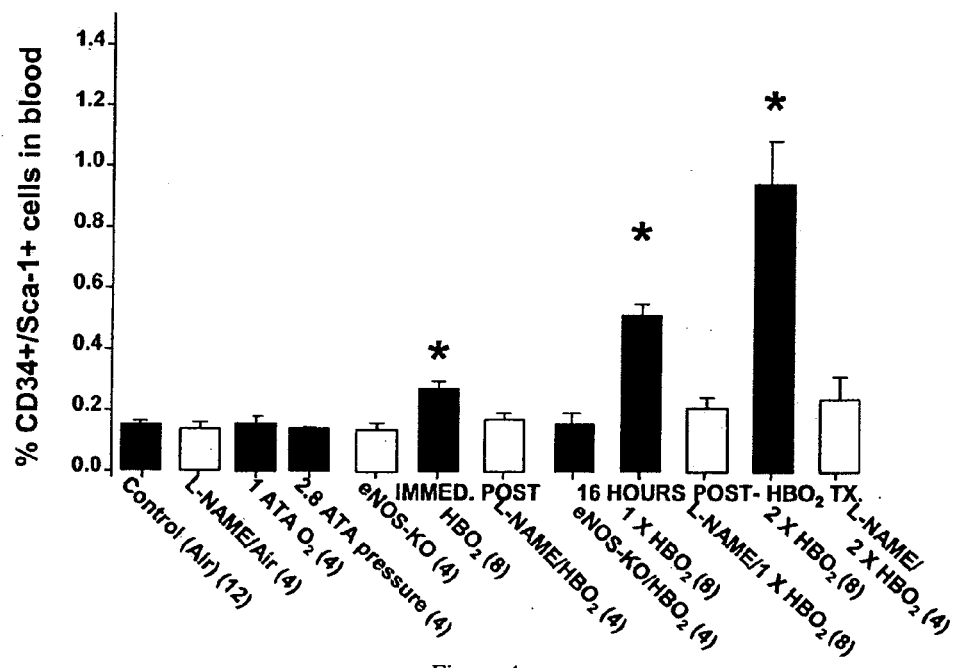
FIG. 4 shows mean CD 34+/Sca-1+ cells in blood from mice undergoing HBO$_2$. From left to right, the bars show: the control conditions (air; L-NAME; oxygen/no-hyperbarics; hyperbarics-air; and eNOS KO-air); the groups with blood collected immediately after HBO$_2$ (without and with L-NAME pre-treatment); the groups with blood collected 16 hrs after a single HBO$_2$ treatment (eNOS KO, wildtype mice, wildtype with L-NAME pre-treatment); and those with blood collected 16 hrs after two consecutive HBO$_2$ treatments (without and with L-NAME pre-treatment), respectively. * One way analysis of variance, p<0.05 versus the control group. (n per group indicated in parenthesis)

In the initial studies searching for the mechanisms for EPC mobilization with HBO$_2$ EPC (assessed as cells that co-expressed CD34 and stem cell antigen-1 (Sca-1)) were also evaluated in peripheral blood of mice. It was subsequently demonstrated (with a number of specific EPC markers in both diabetic and non-diabetic mice models) that HBO$_2$ induces EPC release via a Nitric Oxide mediated mechanism. In preliminary studies, mice were exposed to HBO$_2$ for 90 minutes at up to 2.8 ATA and also to a pressure control, 2.8 ATA pressure using a gas containing 7.5% O$_2$ (so that O$_2$ partial pressure was the same as ambient air, 0.21 ATA O$_2$). In select studies, mice were pre-treated with intraperitoneal L-nitroarginine methyl ester (L-NAME, to inhibit nitric oxide synthase [NOS]), 40 mg/kg i.p. administered 2 hours prior to pressurization). In anesthetized mice, blood was obtained by aortic puncture and bone marrow was harvested by clipping the ends off a tibia and flushing the marrow cavity with 1 ml PBS. Exposure to 2.8 ATA O$_2$ (but not 100% O$_2$ at ambient pressure or 2.8 ATA pressure at a total O$_2$ partial pressure of only 0.21 ATA O$_2$) increased EPC mobilization immediately after treatment, as well as 16 hrs post-treatment, and with repeated treatments (FIG. 4).

There is precedence for rapid mobilization of stem cells from bone marrow, but most emigration is believed to occur after a period of cell proliferation within the marrow niche. It was found that the number of EPC peaked at 16 hours after mice were exposed to 2.8 ATA 100% O$_2$ and if mice were exposed to 2.8 ATA 100% O$_2$ for 90 minutes on two successive days, the number increased even more (FIG. 4). There was no additional increase in peripheral blood EPC if mice were exposed to more than two HBO$_2$ treatments. The leukocyte count in peripheral blood and bone marrow did not increase in response to HBO$_2$ (Table I) but there was a significant elevation in CFCs in both blood and bone marrow, indicating the activation of these cells to grow as colonies with the hyperoxia stimulus.

TABLE I

Data from mice show mean ± SE for studies conducted with air-breathing mice (control) and mice killed 16 hours after one HBO$_2$ treatment (6 mice in each group)

|  | CONTROL | 2.8 ATA O$_2$ |
|---|---|---|
| Blood monocytes/µl | 2,644 ± 306 | 2,103 ± 297 |
| Marrow leukocytes/tibia | 3.2 ± 2.2 × 10$^7$ | 2.9 ± 2.7 × 10$^7$ |
| CFCs/50,000 blood leukocytes | 2.6 ± 0.3 | 4.8 ± 1.4 * |
| CFCs/50,000 marrow leukocytes | 17.0 ± 1.2 | 26.2 ± 1.5 * |
| Plasma SCF (pg/ml) | 42.6 ± 2.8 | 59.5 ± 0.8 * |
| Plasma SCF (pg/ml) if mice pre-treated with L-NAME | 39.4 ± 1.9 | 42.4 ± 2.5 |

* t-test, p = 0.019 for blood CFCs data; p = 0.001 for marrow CFCs data; p = 0.020 for plasma stem cell factor (SCF) data. Mouse SCF was measured using the Quantikine M immunoassay kit from R & D Systems following the manufacturer's instructions EPC mobilization did not occur in mice lacking genes for eNOS (FIG. 4). If wild-type mice were injected before HBO$_2$ with the non-specific nitric oxide synthase inhibitor, L-NAME, EPC mobilization also did not occur (FIG. 4). Soluble kit ligand (skit or stem cell factor, SCF) was significantly elevated in peripheral blood of HBO$_2$-exposed mice and this elevation was also blocked by L-NAME (Table I). These early findings as well as other subsequent extensive data from our laboratory support the view that HBO$_2$ mobilizes EPCs by increasing bone marrow •NO synthesis.

Example 3

HBO$_2$ Increases •NO Concentration in Bone Marrow

Figure 5:
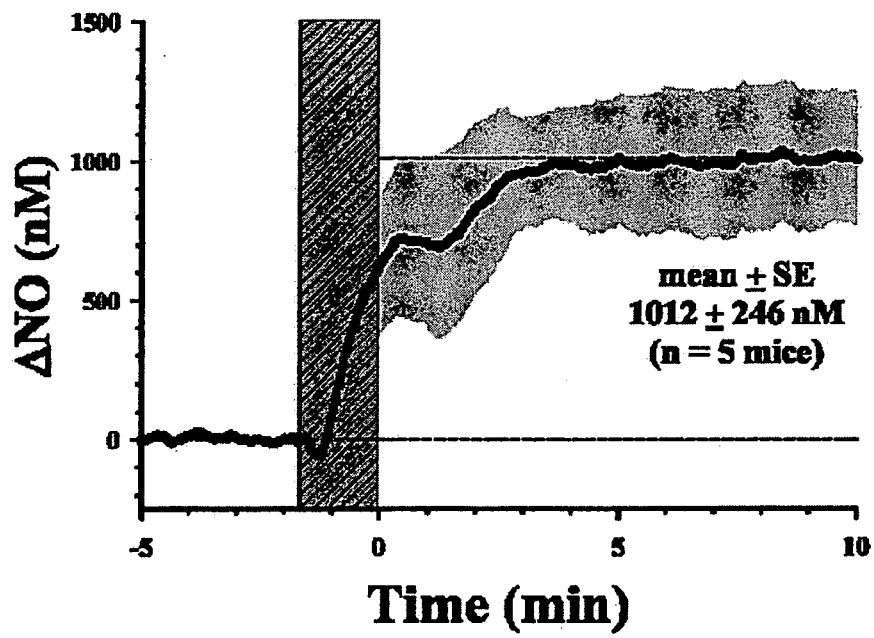
FIG. 5 shows : HBO$_2$ stimulates •NO synthesis in mouse bone marrow. Data show mean and SE is depicted by the grey shading, dark vertical (hatched) shading shows time required to pressurize the mice to 2.4ATA after flushing chamber with 100% O$_2$.

In early studies, it was hypothesized that HBO$_2$ augments stem cell mobilization because it stimulates •NO synthesis in the bone marrow, as •NO is known to play a central role with stem cell release from bone marrow. Anesthetized mice had a small hole drilled into a femur where a •NO specific microelectrode was placed. Mice were placed in a hyperbaric chamber where, while breathing air, baseline measurements were obtained. The chamber was then flushed with 100% O$_2$ and compressed to 2.4 ATA O$_2$. Results (FIG. 5) demonstrated a pronounced elevation of •NO synthesis. If mice were pre-treated with L-NAME (40 mg/kg ip), no •NO signal was detected.

Figure 6:
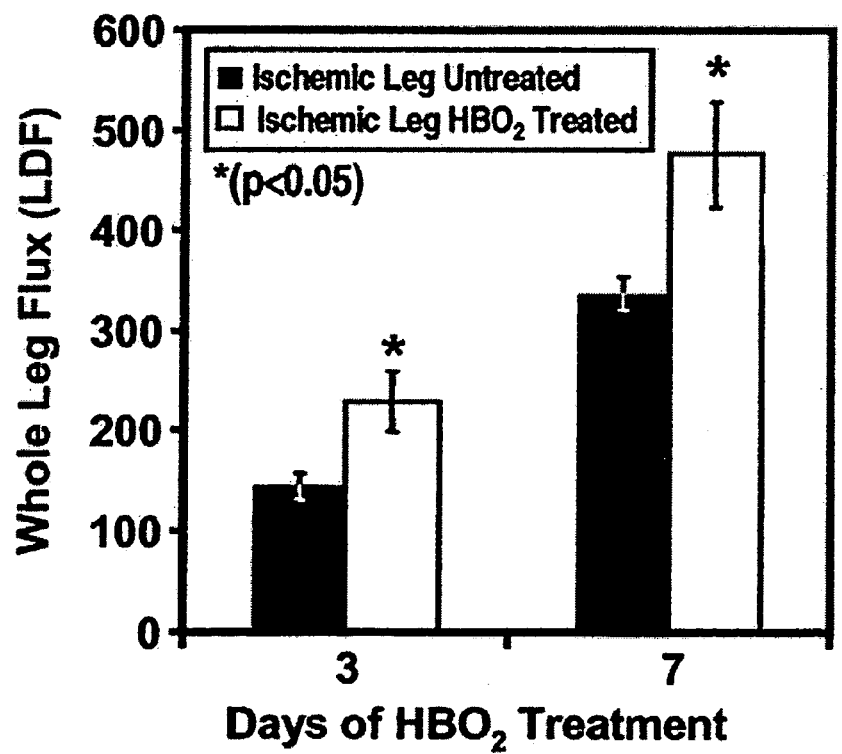
FIG. 6 shows ischemic hindlimb blood flow by LDF is significantly improved in FVB mice by daily HBO$_2$ treatment. Mice underwent femoral ligation and LDF was measured at day 3 and 7 of HBO$_2$ treatment (n=7 mice per group)
Figure 7:
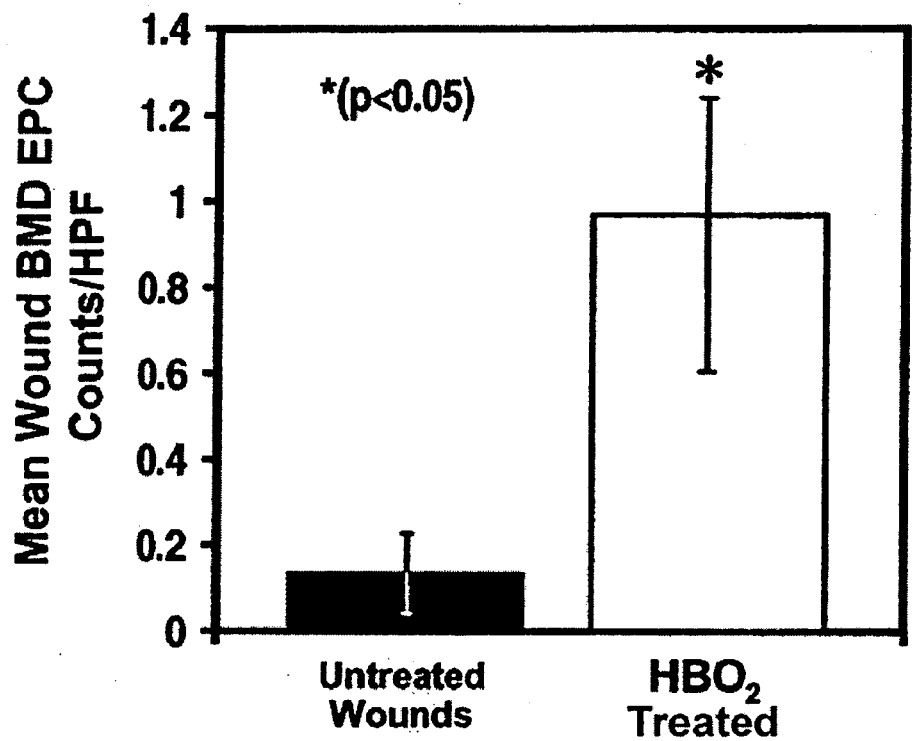
FIG. 7 shows BMD EPC are significantly increased in incisional wounds with daily HBO$_2$ treatment. BMD EPC were tracked to wounds using the FVB/Tie-2-LacZ chimeric mice. Wound biopsies were obtained after 4 HBO$_2$ daily treatments, HBO$_2$ was started on the day of wounding (n=3 mice per group)
Figure 8:
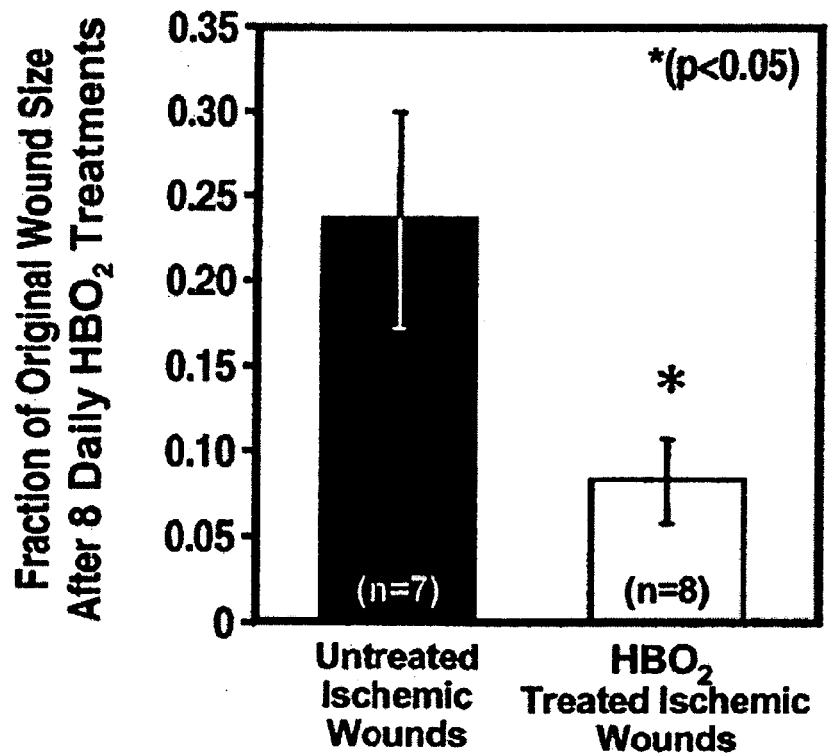
FIG. 8 shows ischemic excisional wounds close significantly faster with HBO$_2$. FBV mice underwent femoral ligation and excisional hindlimb wounds and treated daily with HBO$_2$ for 8 d, starting on the day of wounding. Wound closure was digitally monitored and surface area was calculated using Image J® Software (NIH)
Figure 9:
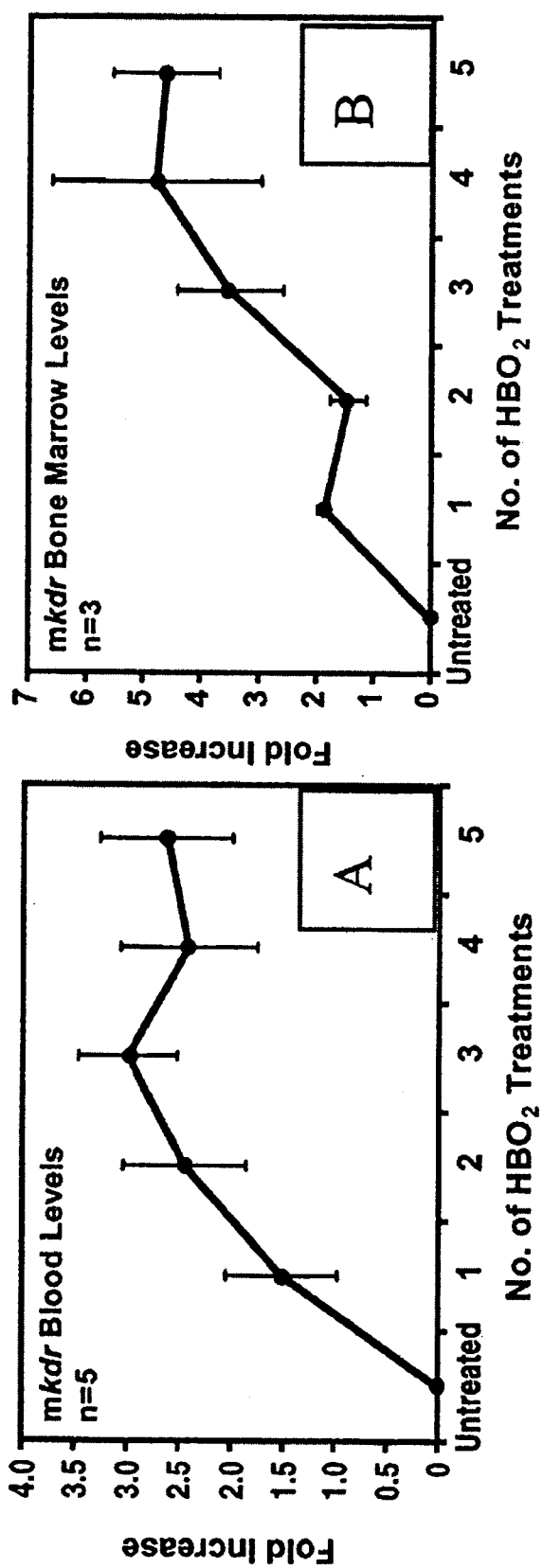
FIG. 9 shows RT-PCR for BMD EPC marker VEGFR-2 (Kdr) after HBO$_2$ in FVB mice blood (A) and bone marrow (B). FVB mice underwent HBO$_2$ treatments and each day blood and bone marrow were collected for VEGFR-2 RT-PCR; n=# of mice per time point; X-axis indicates the number of daily HBO$_2$ treatments; Y-axis shows the relative fold increase in VEGFR-2 mRNA (p<0.05, starting at 2 treatments for blood and 3 treatments for bone marrow)

In addition, it was observed that $HBO_2$ daily treatments (2.4ATA 100% $O_2$ for 90 min) improved hindlimb perfusion by Laser Doppler Imaging (LDF) after femoral ligation/excision (FIG. 6) and increased the bone marrow-derived (BMD) EPC within the incisional wounds, 3 d post-wounding (with 4 $HBO_2$ treatments) (FIG. 7). By day 8 after wounding, ischemic excisional punch biopsy wounds treated daily with $HBO_2$ healed faster (FIG. 8). These wound healing improvements were not observed in mice that received treatment with L-NAME (40 mg/kg i.p.) prior to $HBO_2$, indicating that the improvement in wound healing is mediated by NO. In addition, bone marrow and blood obtained from mice treated daily by $HBO_2$ showed significant increases in the EPC progenitor marker VEGFR-2 mRNA by semi quantitative RT PCR (FIG. 9). FIG. 9 shows data collected from 30 FVB mice that were treated with $HBO_2$ (100% $O_2$ at 2.4 ATA for 90 min, 5 daily treatments). Each day animals were harvested, and blood (retro-orbital bleeding) and bone marrow (flushing of tibias and femurs) collected (3 mice for each time point had bone marrow collected and 5 mice for each time point had blood collected). VEGFR-2 (kdr) mRNA was semi-quantitated by RT PCR. While VEGFR-2 is also present in mature endothelial cells, the acute rise of the marker in bone marrow and blood strongly suggested an $HBO_2$-mediated vasculogenic response. Altogether, the data presented in the examples hereinabove (FIGS. 1-9, Table I) indicated that EPC mobilized by $HBO_2$ are likely functional, and that $HBO_2$ mediates effects on endothelial progenitor cells via NO mechanisms.

Example 4

BMD EPC Contribute to Wound Healing

Figure 10:
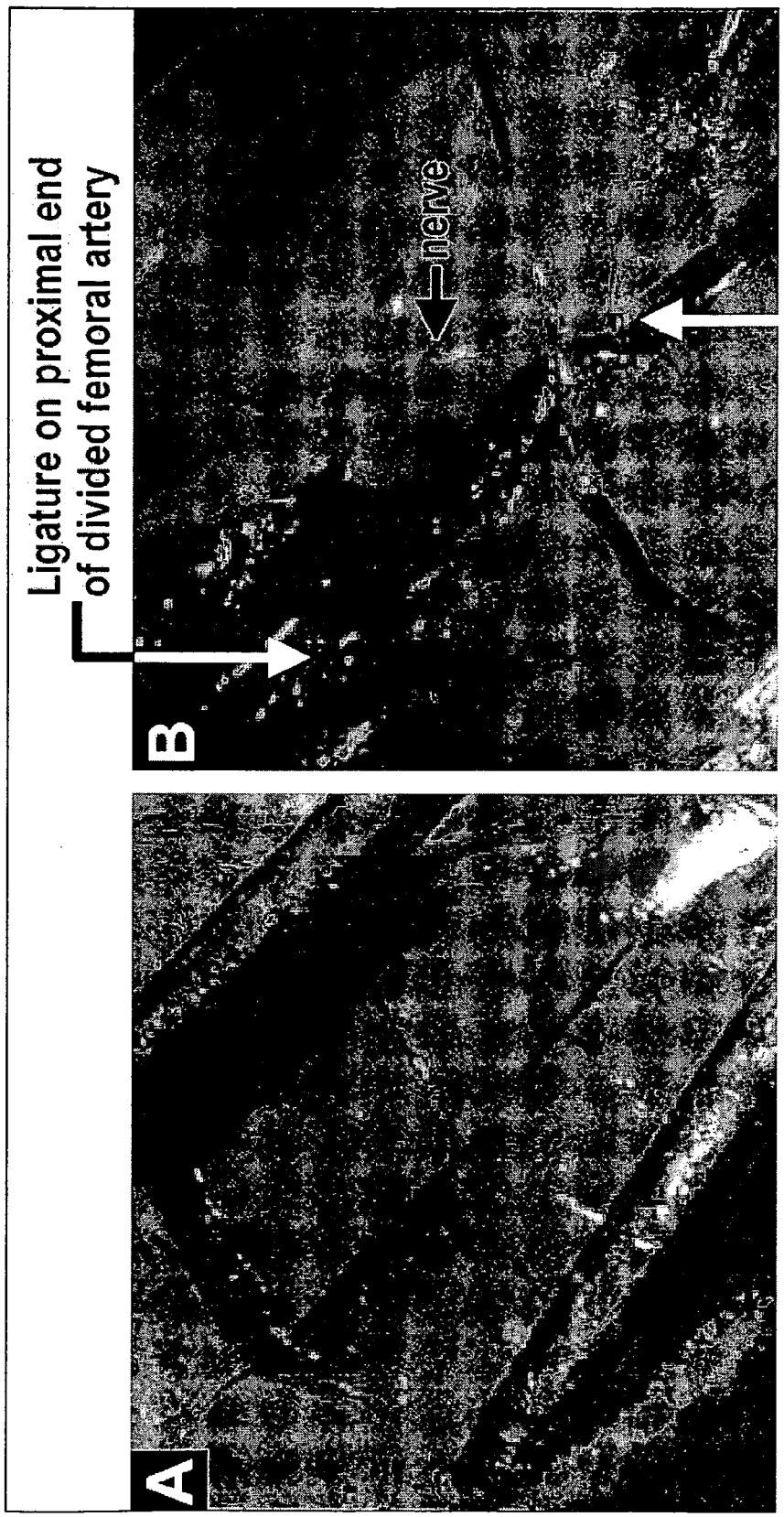
FIG. 10 shows murine femoral ligation model. (A) Exposure of femoral neurovascular bundle and (B) Dissection of the femoral vein and nerve away from the artery with selective femoral artery ligation/excision in FVB mouse.
Figure 11:
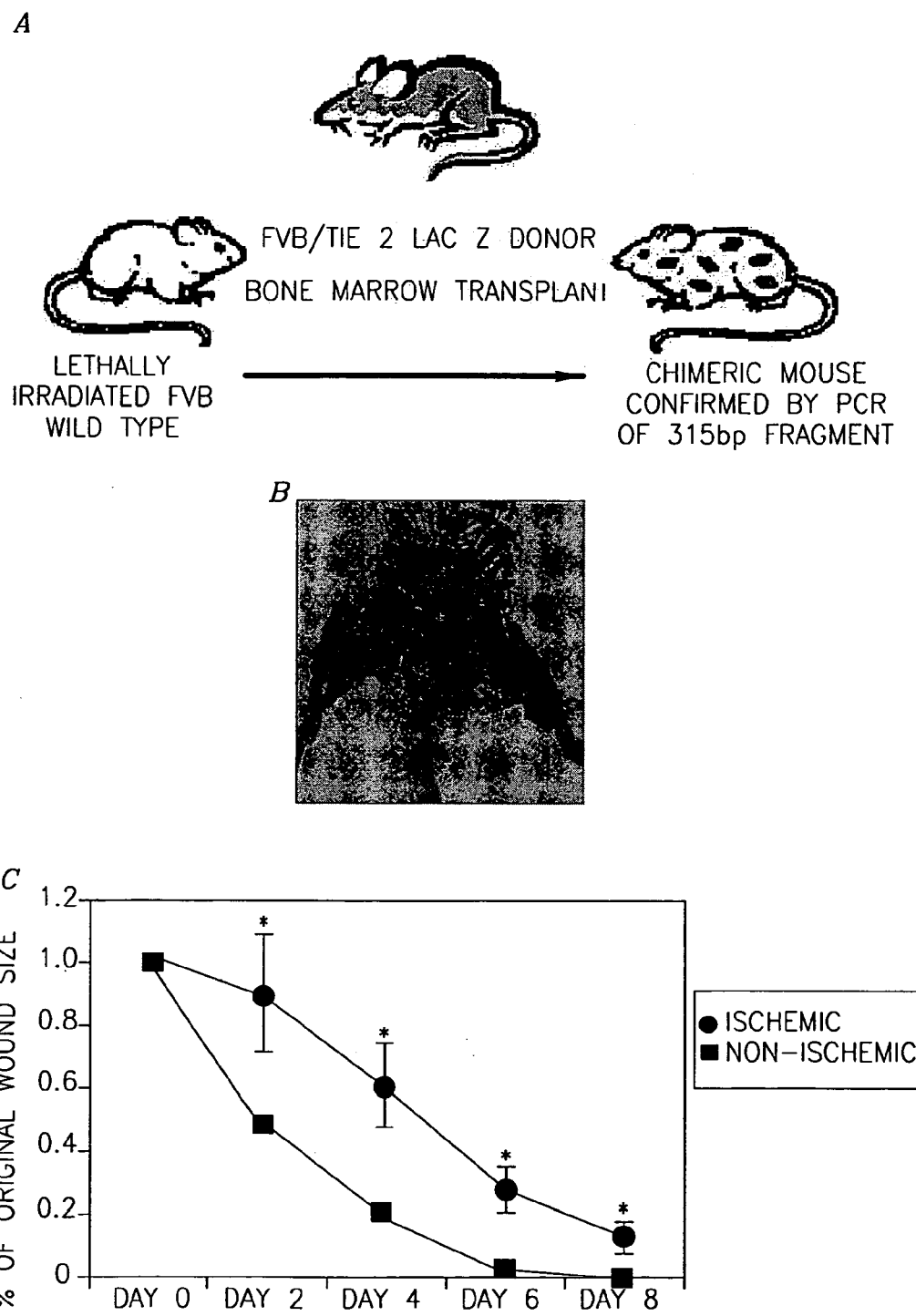
FIG. 11 shows flow cytometry data from one patient before and after the 1st and 10th HBO$_2$ treatment.
Figure 11:
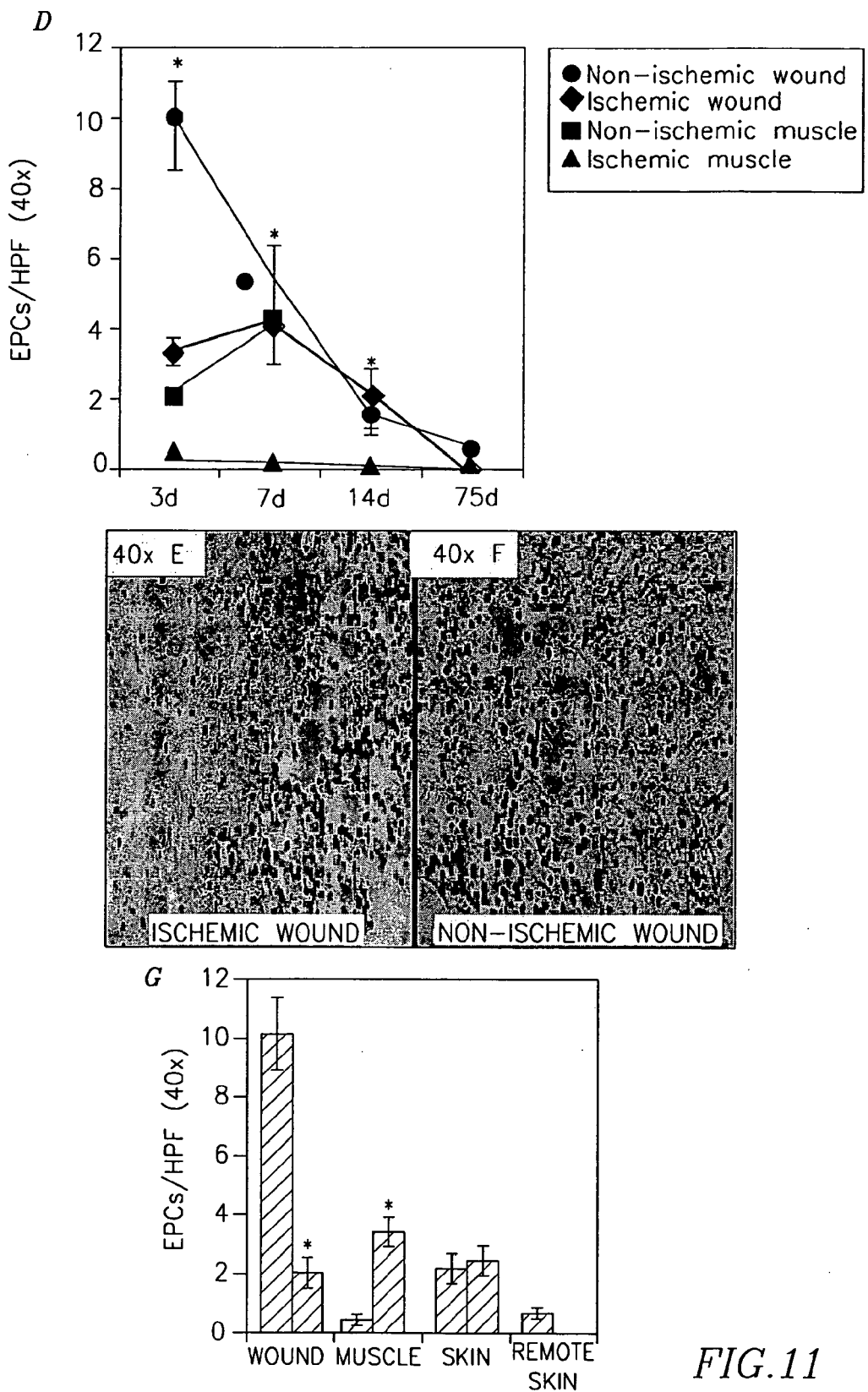

BMD EPC contribute to wound healing since these progenitor/stem cells are the key cellular effectors of post-natal vasculogenesis. BMD EPC given to animals with surgically induced limb ischemia incorporate into foci of neovascularization in ischemic muscle, skin, and wounds. A critical role for BMD EPC in ischemic wound healing was identified. The contribution of bone marrow-derived endothelial progenitor cells to wound healing was quantified with and without ischemia in chimeric mice formed using bone marrow from FVB/Tie-2-LacZ transgenic mice (FVB/N-TgN[TIE2LacZ] 182Sato, The Jackson Laboratory, Bar Harbor, Me.). Tie-2-LacZ mice are well suited for specifically tracking bone marrow-derived progenitor cells of the endothelial cell lineage because the endothelial-specific Tie-2 promoter is linked to the LacZ reporter gene allowing cells to be identified by β-galactosidase (β-gal) expression. After creating the chimeric mice (as depicted in FIG. 11A), a murine model of hind limb ischemia induced by femoral ligation/excision was used, (as depicted in FIG. 10). Hindlimb ischemia was monitored using laser doppler flowmetry (LDF) that allows for quantifying cutaneous blood flow in the ischemic relative to the nonischemic hind limb. Hindlimb ischemia resulted in delayed wound healing (FIG. 11 A-C). Acutely healing wounds in non-ischemic hind limbs were then compared with delayed healing wounds in the contralateral ischemic hindlimb and correlated healing rates to BMD EPC recruitment into wounds. It was determined that BMD EPC play a key role in wound healing and are recruited into the granulation tissue of acutely healing (non-ischemic) wounds in significantly greater numbers than to delayed-healing (ischemic) wounds (FIG. 11 D-G). These studies show that BMD EPC contribute to acute wound healing and the process is deficient or incomplete at the level of skin wounds, in the presence of severe ischemia.

In diabetic patients and diabetic murine models, the number and function of circulating BMD EPC are severely impaired and this defect is highly correlated with the long-term cardiovascular and wound healing complications seen in Diabetes. Increasing evidence suggests that wound healing mechanisms, in both the bone marrow and within the peripheral wound, are compromised by diabetes as a result of BMD EPC impairments. While cytokines (e.g. Granulocyte Colony-stimulating Factor (GM-CSF) and growth factors (e.g. Vascular Endothelial Growth Factor-A (VEGF-A)) can induce the release of progenitor cells from the bone marrow, the non-specific effects on release of other white cells and platelets or the leaky-capillary effect has made these factors unsuitable to treat diabetic patients with non-healing chronic wounds.

Example 5

Impaired Phosphorylation of BM eNOS in Diabetic Mice

Figure 12:
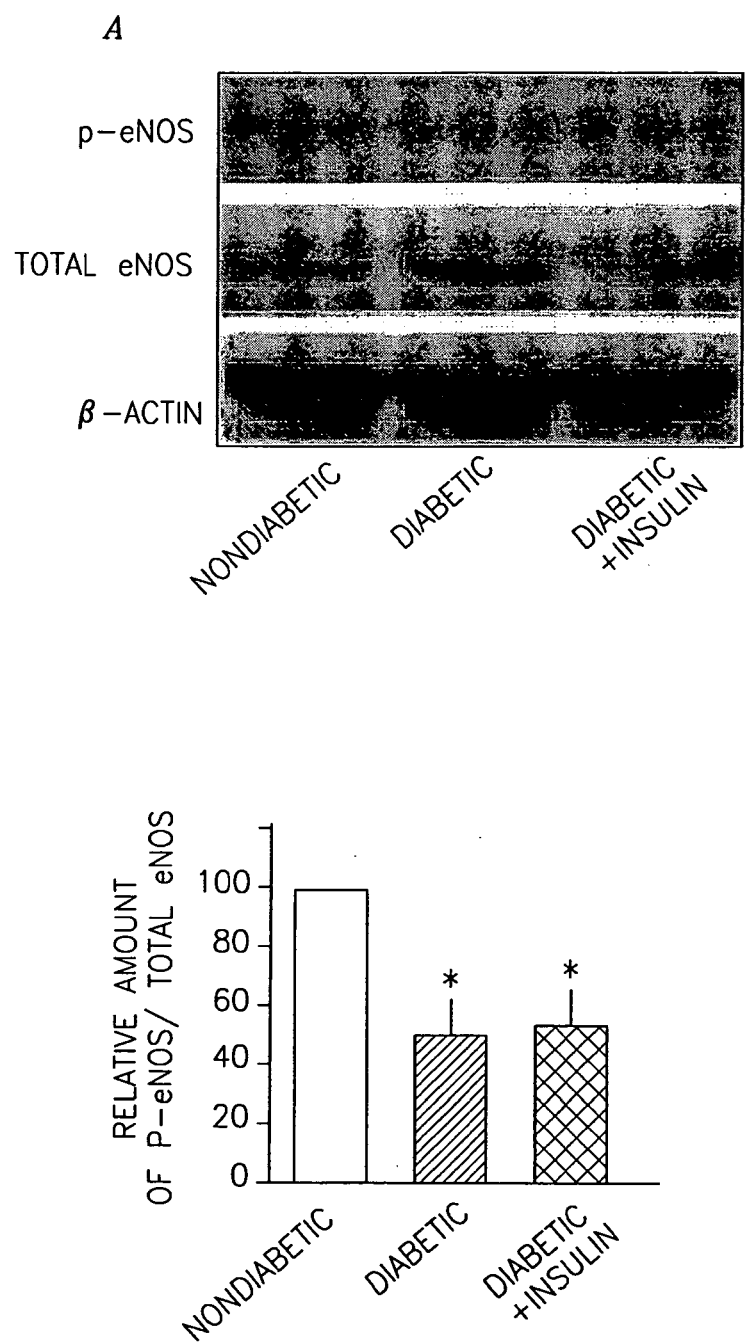
FIG. 12 shows impaired phosphorylation of BM eNOS with attenuation of HBO-induced NO levels results in decreased circulating EPCs in diabetic mice. (A) Representative Western blot analysis for BM eNOS. Diabetic mice demonstrated decreased phosphorylated eNOS compared with nondiabetic controls. Insulin failed to restore impaired eNOS phosphorylation. Quantification of phospho-eNOS (p-eNOS). Results are based on 4 experiments and show the amount of phospho-eNOS relative to total eNOS and β-actin. Nondiabetic controls are used as the standard (value set at 100). *P<0.01. (B) Changes in cell composition in BM of diabetic mice. EPC (VEGFR2/CXCR4) and HSC (CD34/CD45) populations are unchanged, while mesenchymal stromal (CD73/CD44) and inflammatory cell (SSC/CD3/CD45RA) populations are slightly decreased in diabetic mice compared with nondiabetic mice. Percentages indicate positive cells in total BM cells counted. (C) Quantification of the number of Tie2+/VEGFR2+EPCs/µl of peripheral blood in Tie2-GFP mice by flow cytometry at 7 days following STZ treatment. A substantial reduction in circulating EPCs was found in diabetic compared with nondiabetic mice. (D and E) NO production in the BM cavity of diabetic and nondiabetic mice during 10 minutes of HBO treatment. Baseline NO levels were obtained 5 minutes prior to onset of pressurization at 100% O$_2$ (gray bar). Solid lines represent mean values, with surrounding gray or black shading representing SEM. (D) Hyperoxia increases BM NO levels significantly, but the NO response is attenuated in diabetic mice compared with non-diabetic animals (P<0.05). Insulin did not reverse the impairment of NO production. (E) Total iNOS and nNOS proteins were upregulated in diabetic mice. −, nondiabetic mice; +, diabetic mice. (F) Complete inhibition of BM NO production in diabetic and nondiabetic mice undergoing HBO treatment after pretreatment with 1-NAME.
Figure 12:
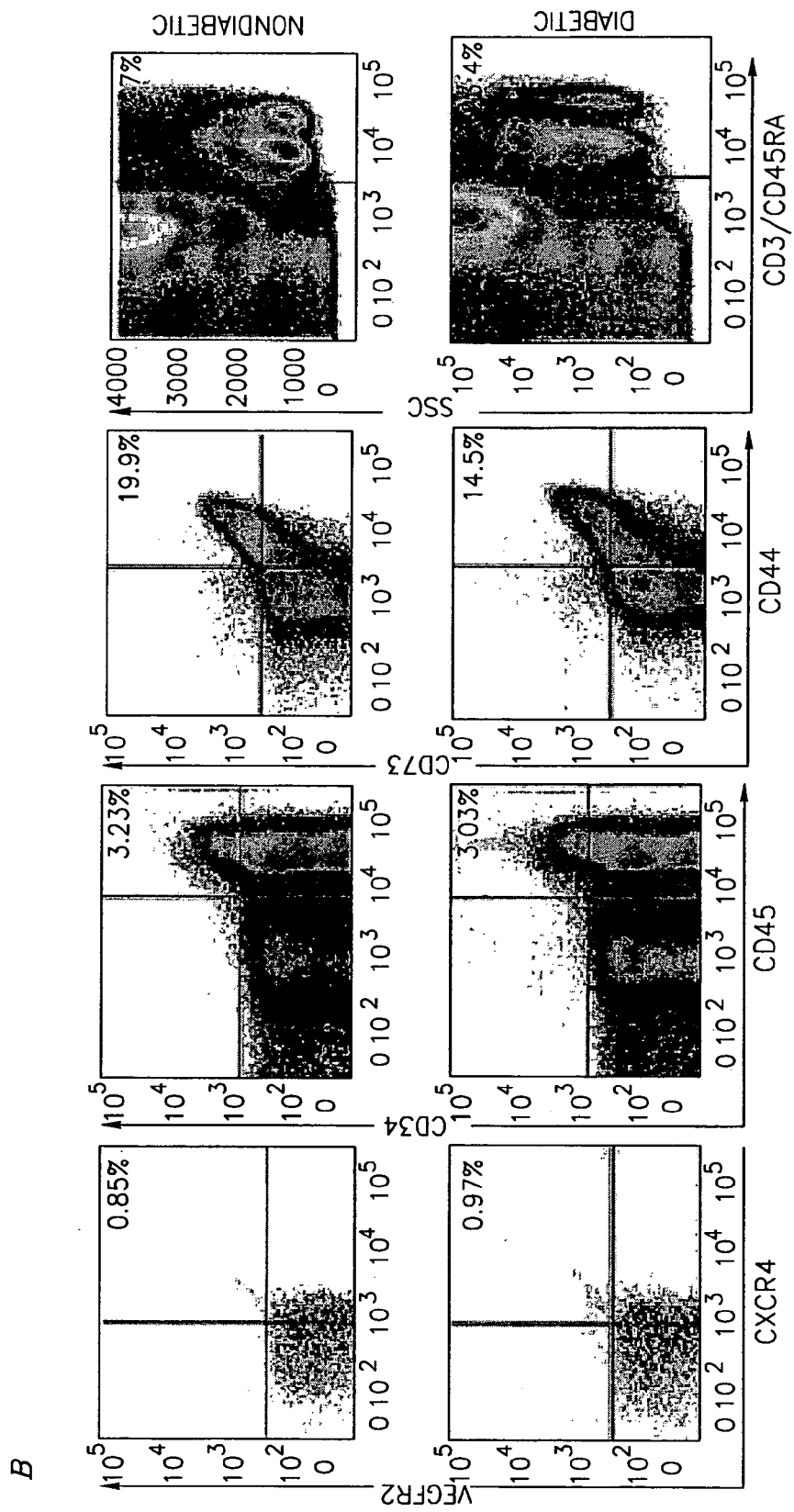
Figure 12:
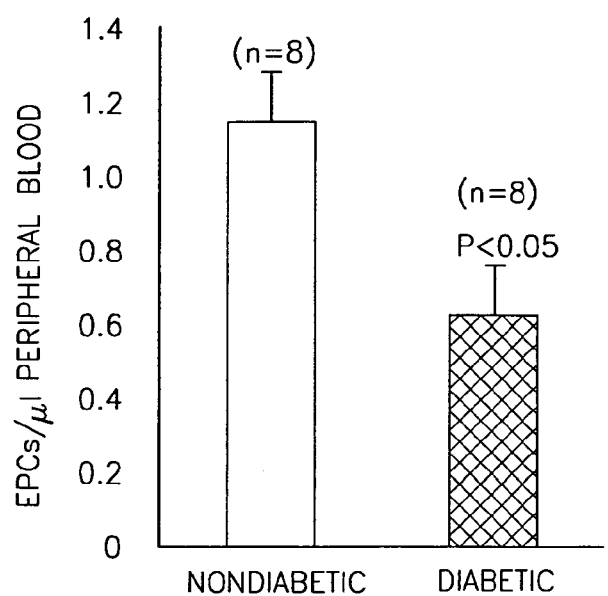
Figure 12:
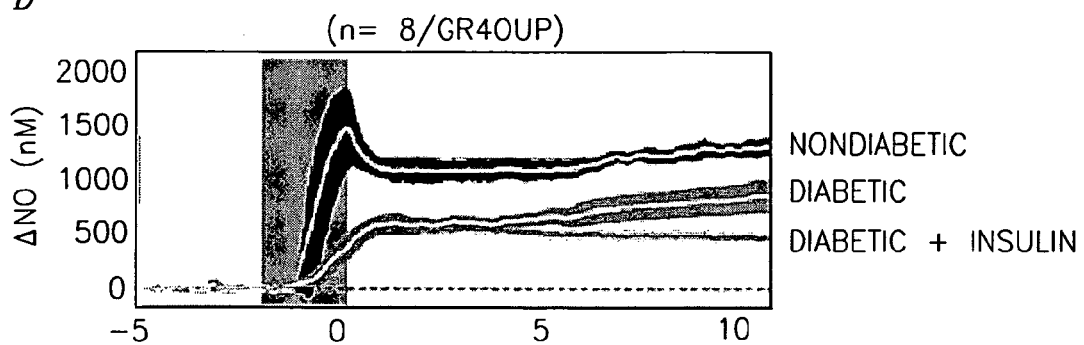
Figure 12:
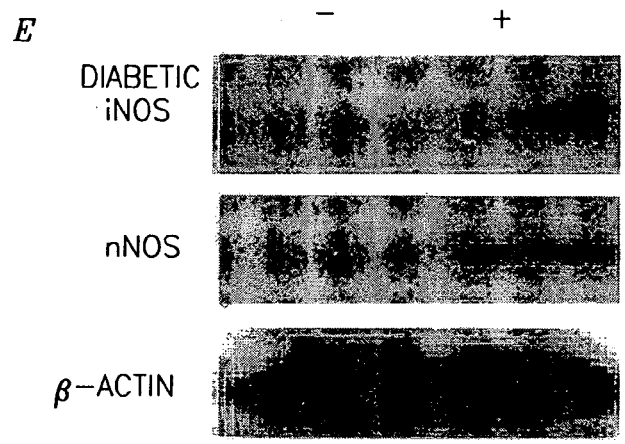
Figure 12:
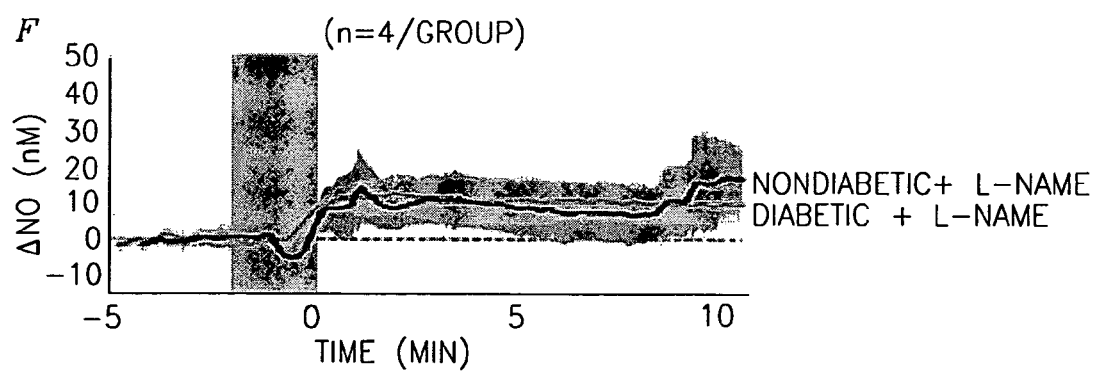

In diabetic patients, circulating EPCs are decreased in both number and function, and so it was hypothesized that BM eNOS activation is impaired in diabetes. To examine this question, BM was isolated from streptozocin-induced (STZ-induced) diabetic and nondiabetic mice and analyzed via Western blot for levels of total and phosphorylated eNOS protein. Although no changes in the amount of total eNOS protein were observed, the levels of biologically active phosphorylated eNOS protein were decreased in diabetic mice as compared with nondiabetic controls (FIG. 12A). To investigate whether the decreased eNOS activity might reflect a change in cellular composition within BM of diabetic mice, the constitution of EPCs, stromal cells, HSCs, and lymphocytes was studied in the BM of STZ-induced diabetic versus nondiabetic mice. The EPC and HSC populations remained constant while the mesenchymal stromal cell and lymphocyte populations demonstrated a slight decrease (by approximately 27% and 26%, respectively) in diabetic compared with nondiabetic mice (FIG. 12B). Thus, it is evident that diabetes-induced changes in mesenchymal stromal cell and lymphocyte populations in the BM might be responsible for the observed downregulation of BM eNOS activation.

Example 6

Circulating EPCs are Decreased in Diabetic Mice

Given the central role of eNOS on EPC mobilization and the results in Example 5 demonstrating impaired eNOS phosphorylation in diabetic BM, the hypothesis that circulating EPCs are decreased in diabetic mice was tested. Our findings demonstrate that diabetic mice have an approximately 50% reduction in circulating EPCs as compared with nondiabetic controls (FIG. 1C). Hence, impairment in the phosphorylation of eNOS to its biologically active form likely results in depressed mobilization of EPCs from BM into peripheral circulation.

Example 7

Hyperoxia-Induced Stimulation of BM NO Production is Attenuated in Diabetic Mice Physiologically, the NO-mediated EPC release into circulation occurs in response to tissue-level hypoxia, although this compensatory response is inadequate in the setting of diabetes and results in severe defects in neovascularization and wound healing. Interestingly, it was determined that hyperoxia is a non-physiologic stimulus that increases EPC mobilization via a similar NO-mediated mechanism. Therefore, it was sought to utilize HBO as a tool to augment EPC release into circulation and further study both EPC mobilization and wound-homing mechanisms in the presence of diabetes. The goal was to determine whether hyperoxia stimulates NO production in the BM of diabetic mice via a NOS-mediated pathway and whether this pathway is impaired in diabetes. To test this hypothesis, Nafion polymer—coated NO microsensors were inserted into the femur BM space of both STZ induced diabetic and nondiabetic mice to measure real-time NO levels within the BM prior to and is during HBO-induced hyperoxia. As predicted, diabetic mice demonstrated a significantly attenuated rise in BM NO in response to hyperoxia (FIG. 12D). Despite this attenuated response, significant increases from baseline were still observed in BM NO levels in response to hyperoxia in the diabetic mice. Specifically, diabetic mice demonstrated an 800-fold increase in BM NO levels during hyperoxic therapy, as compared with a 1,200-fold NO rise in nondiabetic controls. It was speculated, that this was likely due to a compensatory effect from other NOS isoforms, and therefore the level of both iNOS and nNOS was examined in diabetic mice. As anticipated, the expression of both total iNOS and nNOS protein was upregulated in diabetic mice (FIG. 12E). However, no observation was made of any changes in the phosphorylation of these NOS isoforms. These data show that upregulated NOS isoforms require additional stimuli, such as hyperoxia, to be activated in diabetic mice. Consistent with this, hyperoxia-induced increases in NO production were completely inhibited in both the diabetic mice and the nondiabetic controls by pretreatment with N-nitro-1-arginine-methyl ester (1-NAME), a nonspecific NOS inhibitor that inhibits all 3 isoforms of the NOS enzyme (FIG. 12F). Hyperbaric normoxic pressurized and hyperoxic nonpressurized control conditions were also studied and demonstrated no increase in BM NO production (data not shown), confirming that hyperoxia is the key stimulus for the BM NOS activation Example 8

Figure 13:
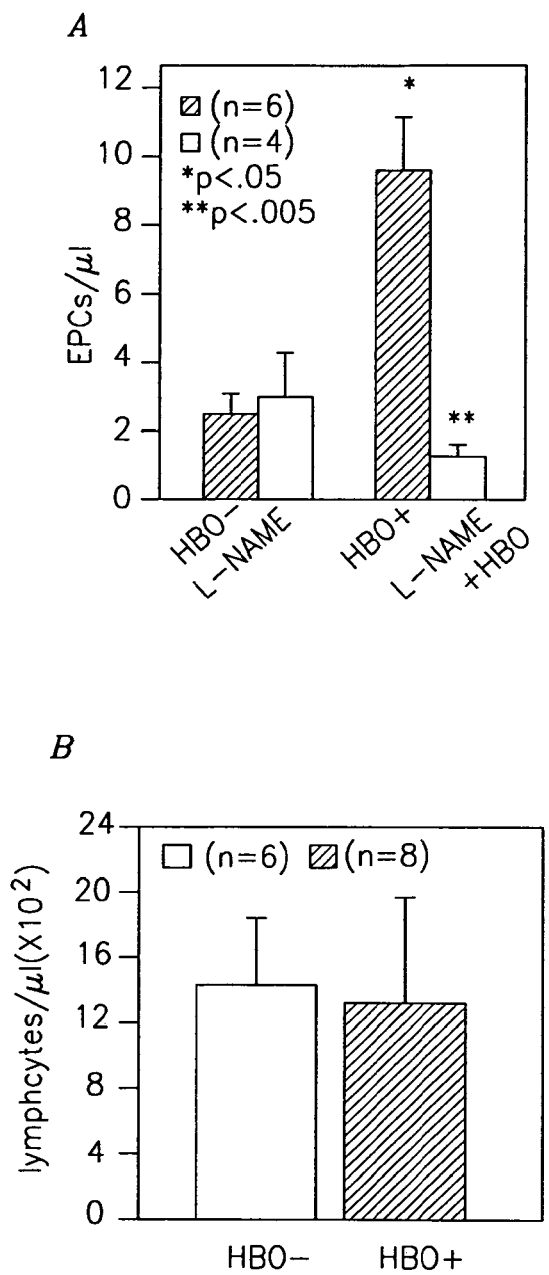
FIG. 13 shows NO-dependent EPC, not lymphocyte, mobilization is enhanced by hyperoxia. Flow cytometry quantification of circuiting EPCs (CXCR4$^+$/VEGFR2$^+$) (A) and lymphocytes (B) in FVB and EPCs (Tie2$^+$/VEGFR2$^+$) in Tie2-GFP (H) mice. Data are based on 6 (A) and 12 (H) experiments. Mice treated with HBO±, or L-NAME± HBO. HBO significantly increased circulating EPC and L-NAME inhibited this effect. Representative dot plots with circuiting EPC number in diabetic FVB (C-G), nondiabetic (I-L) and diabetic (M-P) Tie2-GFP mice. (C, I, M): HBO−; (D, J, N): HBO+; (E, K, O): L-NAME; and (F, L, P): L-NAME+HBO. (G) isotype control (VEGFR2/CXCR4)
Figure 13:
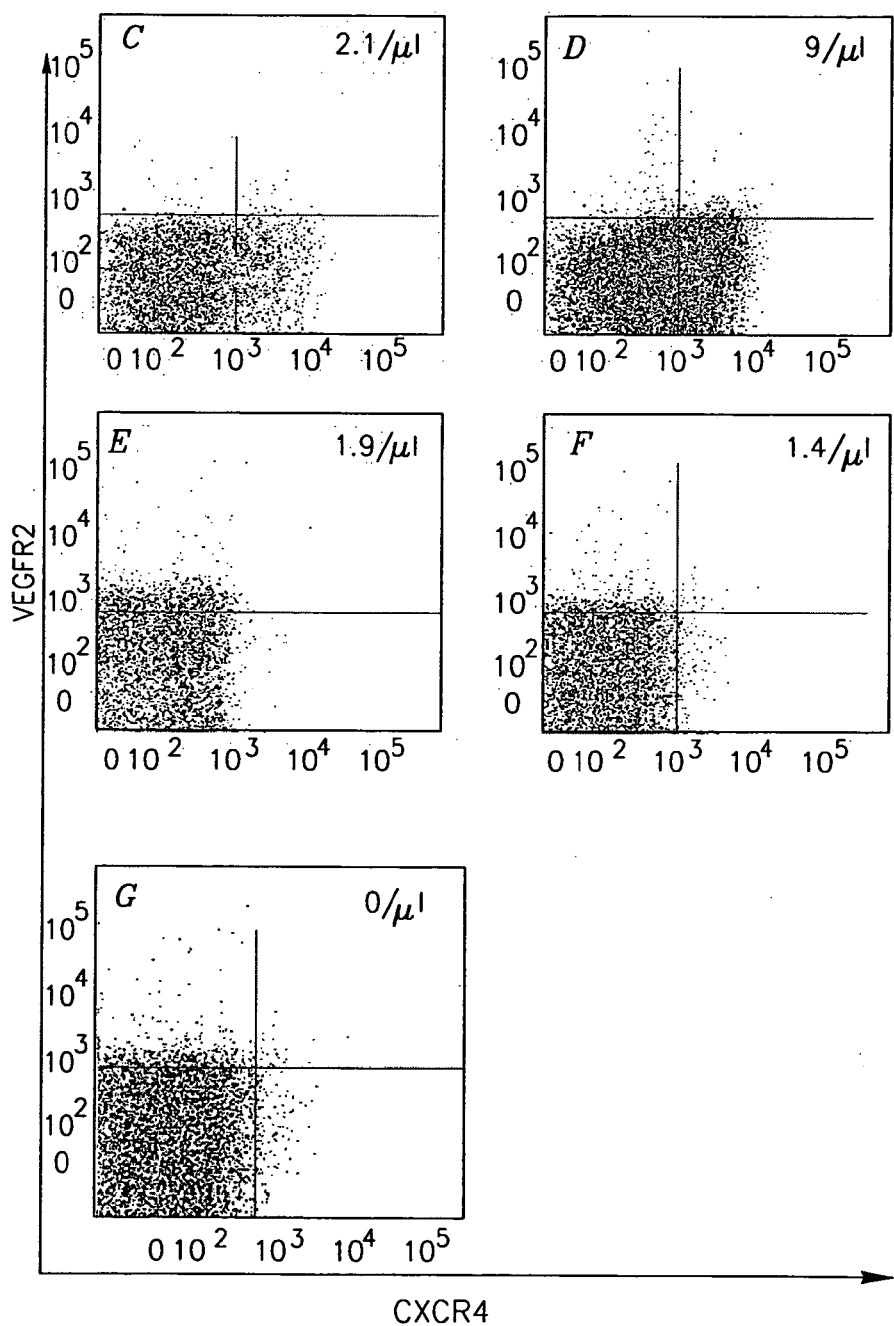
Figure 13:
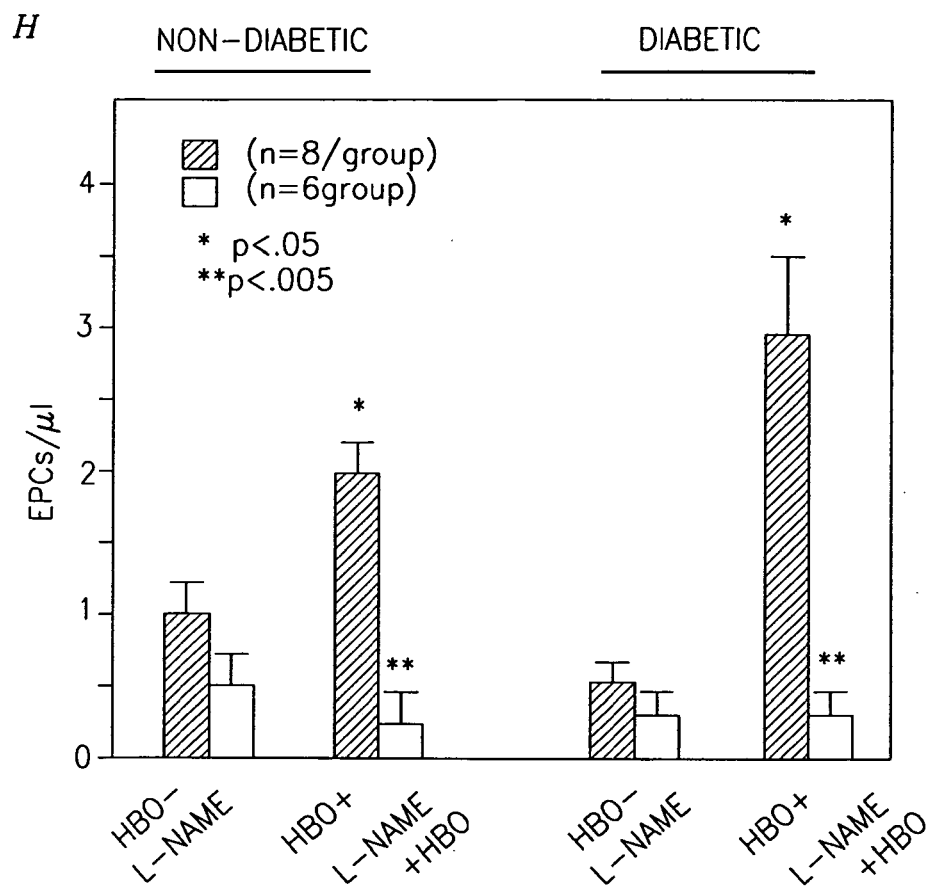
Figure 13:
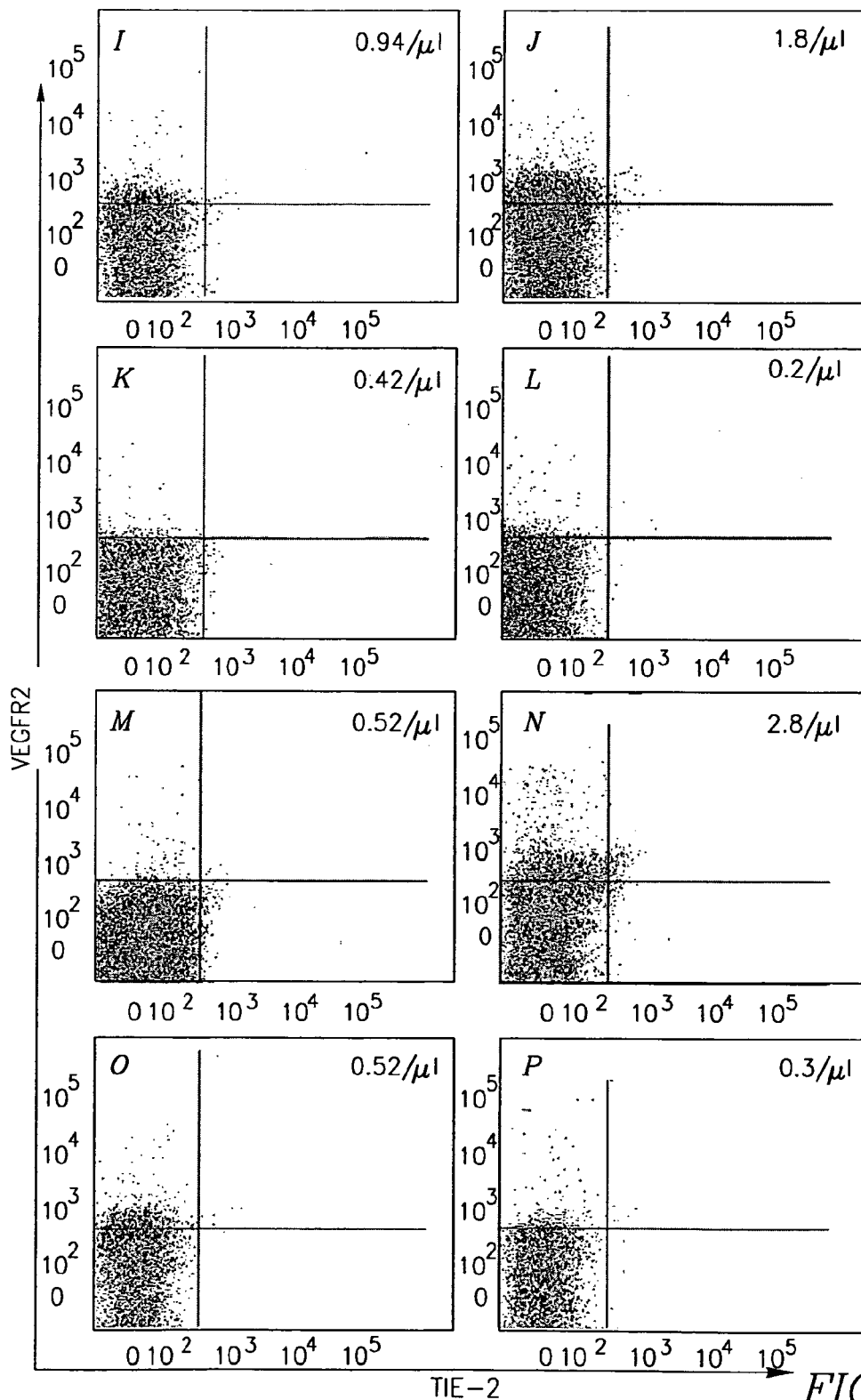

Increases in BM NO Induced by Hyperoxia Stimulate Mobilization of BM EPCs into Peripheral Circulation in Diabetic Mice Physiologically, increased levels of BM NO result in activation of MMP-9 and conversion of kit ligand to its soluble form, ultimately generating EPC release into circulation. To study the effects of the hyperoxia-induced rise in NO levels in the marrow cavity on mobilization of EPCs into circulation, peripheral blood from diabetic mice was analyzed for EPCs using flow cytometry. A determination of whether hyperoxia, induced by HBO, increases the number of circulating EPCs in the peripheral blood of diabetic mice was made. Specifically, peripheral blood of diabetic mice was examined 18 h after a single HBO treatment. After excluding dead DAPI+labeled cells, candidate lymphocytes, identified by their typical appearance on forward and side scatter, were gated and CD45+/CD3+cell populations were excluded. Although EPC markers in humans are well established, the markers that are present on murine EPCs have yet to be precisely defined. Therefore, several marker combinations were used to quantitate circulating EPCs. In independently repeated experiments, EPCs were identified as cells double-labeled with either Tie2 and VEGFR2 or CXCR4 and VEGFR2. Following treatment with hyperoxia, diabetic mice demonstrate a significant 5-fold increase in circulating CXCR4+/VEGFR2+ EPCs and Tie2+/VEGFR2+EPCs (FIG. 13). Nondiabetic mice treated with HBO showed a similar increase in circulating EPCs, however, the effects of hyperoxia on EPC mobilization were less pronounced as a result of the higher baseline circulating EPC level in the nondiabetic animals. Unlike EPCs, the numbers of circuiting lymphocytes were constant before and after HBO treatment (FIG. 13B), indicating that hyperoxia does not affect lymphocyte mobilization in diabetic mice. In order to specifically determine if the hyperoxia-induced EPC mobilization is the result of NOS activation, a group of mice were treated with L-NAME prior to HBO. No increase in EPC mobilization following HBO treatment was observed in any of the L-NAME pre-treated animals. This data demonstrates that hyperoxia, via an NO-mediated mechanism, increases mobilization of EPCs from BM into circulation and reverses the pre-existing circulating EPC deficit in diabetes, thus improving the numbers of EPCs potentially available for vasculogenesis and wound healing. However, despite the ability of hyperoxia to increase circulating EPCs, there was no significant increase in the numbers of EPCs homing to diabetic wounds in response to HBO treatment (see FIG. 16A), confirming prior observations that recruitment of EPCs from circulation to peripheral tissue in diabetes is impaired. Thus, it was hypothesized that unfavorable local wound conditions, such as decreased levels of the key EPC homing chemokine, SDF-1α, may explain the diabetic EPC-homing defect, and hence, the disparity between circulating EPC numbers and wound-level EPCs in HBO treated diabetic animals.

Example 9

SDF-1α Expression is Decreased in Diabetic Peripheral Cutaneous Wounds

Figure 14:
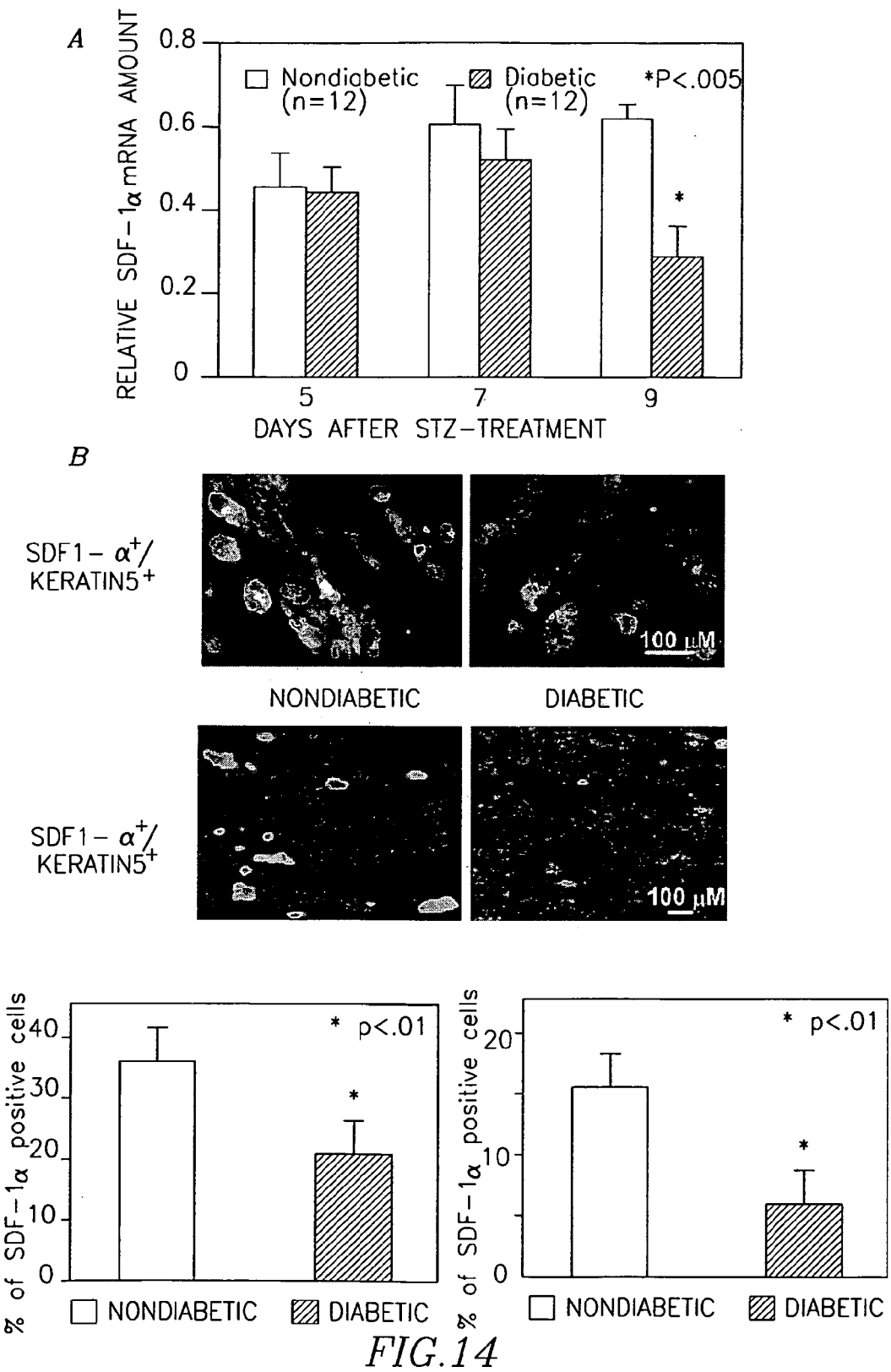
FIG. 14 shows decreased SDF-1α expression in peripheral wounds of diabetic mice. (A) Quantitative detection of the SDF-1α mRNA at various time points post-STZ treatment in wound tissue of diabetic versus non-diabetic mice by real-time RT-PCR. SDF-1α mRNA decreased significantly at d 9 post-STZ treatment. Data are based on 3 experiments. (B) Stromal cells are the source of SDF-1α in the wound tissues. Double staining of SDF-1α (red) and cell type-specific marker (green) demonstrated a downregulated expression of SDF-1α in stromal cells in diabetic wounds.
Figure 19:
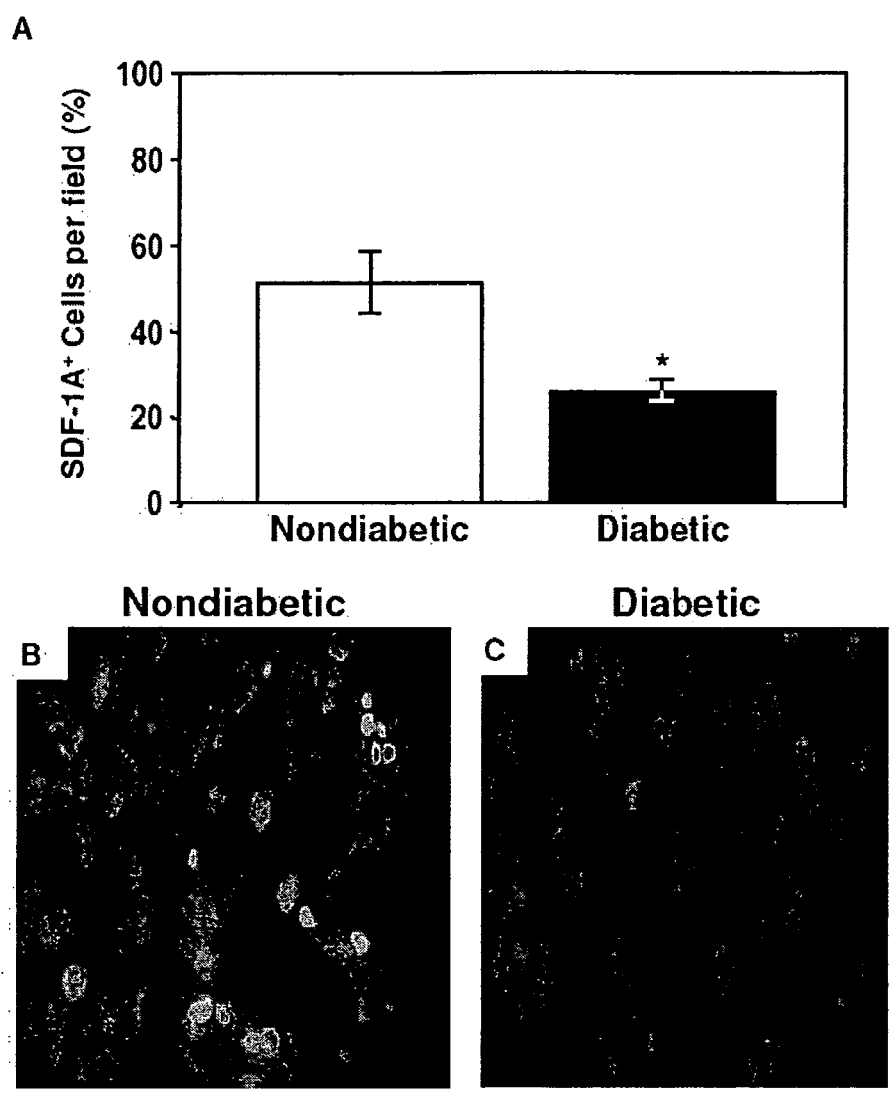
FIG. 19 shows decreased numbers of SDF-1α$^+$ expressing cells in peripheral wounds of diabetic mice. (A) Wounds were examined for SDF-1α$^+$ expression in diabetic (n=5) and nondiabetic (n=5) mice by fluorescence immunostaining 24 h post-wounding. For each animal, the percentage of cells expressing SDF-1α was quantified relative to the total wound cellularity in 5 serial cross-sections per wound, counting 10 random high power fields (HPF) at 100× magnification. Wounds harvested from diabetic mice demonstrated significantly fewer cells expressing SDF-1α as compared to nondiabetic controls. *$P<0.005$. (B-C) Representative SDF-1α$^+$ staining of wound sections of nondiabetic (B) and diabetic (C) animals are shown. Sections (5 μm thick) were stained for cells with anti-SDF-1α antibody and Alexa 488-conjugated secondary antibody (green). Nuclei were counterstained with Hoescht dye (blue)
Figure 20:
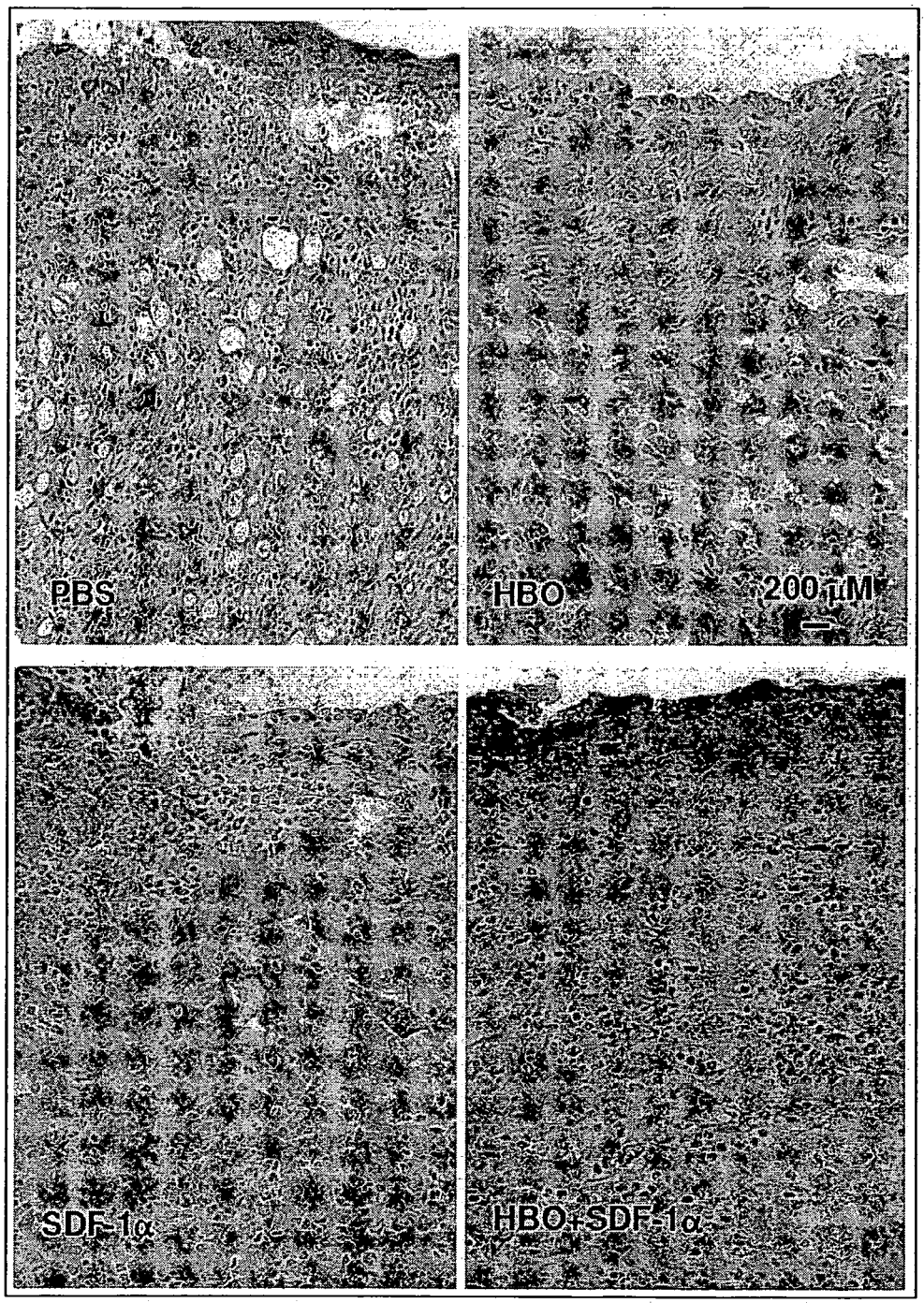
FIG. 20 shows H&E staining showed overall stromagenesis in healing wounds at d 6. SDF1α+HBO treatment enhances stromagenesis most strongly compared to other group.

Physiologically, SDF-1α is one of the primary chemokines responsible for the mobilization and homing of EPCs to ischemic tissue. SDF-1α expression is induced in a wide variety of cell types in response to stimuli such as stress and injury. The role of SDF-1α in diabetes-related chronic wounds has not been previously studied. Current thinking indicate that in diabetes, the impaired neovascularization and delayed healing of cutaneous wounds is, at least in part, due to the reduced number and function of EPCs, but it is likely that other tissue-level factors contribute to poor wound healing in diabetes. To examine this issue, whether the diabetic phenotype is associated with a decreased expression of SDF-1α in wound granulation tissue was investigated. Peripheral wound tissue from both diabetic and nondiabetic mice at various time points (d 5, 7 and 9 post-STZ treatments) was harvested and examined using quantitative real-time RT-PCR. Our results demonstrate that SDF-1α decreased significantly (−50%) at d 9 post-STZ treatments (FIG. 14A). Moreover, fluorescent microscopy for cells expressing SDF-1α, 10 d after STZ treatment and 24 h after initial wounds were created. Approximately half as many cells from diabetic wounds expressed SDF-1α as compared to wound cells from nondiabetic mice (FIG. 19). To identify the type(s) of cell(s) as the source of SDF-1α in diabetic wound lesion, a series of double-staining (SDF-1α and cell type specific antigen) was performed to examine myofibroblasts (α-SMC actin), epithelial cells (keratin 5), inflammatory cells (CD3/CD4), and ECs (CD31). Number of cells appear to be responsible for the downregulation of SDF-1α in diabetic wound lesion (FIG.

14B). Thus, in diabetic tissue, decreased expression of SDF-1α by cells may account for the lack of homing of EPCs to peripheral wounds, despite the increased systemic release of these cells after HBO treatment. These findings suggested a novel therapeutic target in diabetic wound healing.

Example 10

HBO and SDF-1α Synergistically Increase Circulating EPCs in Diabetic Mice

Based on the findings that SDF-1α expression in peripheral tissue is decreased in diabetes, a study of the effects of exogenous administration of SDF-1α, via local wound injections (both alone and in combination with HBO), on EPC mobilization, tissue homing and wound healing, in diabetic mice was carried out. It was hypothesized a potential synergism on EPC tissue-level homing and wound healing using HBO and SDF-1α as combined therapeutic strategies. Interestingly, enhanced EPC mobilization was observed in the SDF-1α and HBO treated diabetic animals. Hyperoxia was theorized to enhance EPC mobilization and SDF-1α wound injections, while minimally impacting the number of circulating EPCs, and increase homing to diabetic wounds. Confirming previous findings, tissue-level hyperoxia was shown to induce an increase in the mobilization of EPCs into circulation in wounded diabetic mice, assessed by flow cytometry of the peripheral blood for cells co-expressing CXCR4 and VEGFR2 (FIG. 15A-B). In these mice, HBO treatment resulted in an approximate 4-fold increase in the percentage of circulating EPCs. Interestingly, local wound injections of SDF-1α resulted in a 2-fold rise in EPCs in circulation. Perhaps most striking, the combination of HBO and peripheral wound SDF-1α administration resulted in a synergistic 11-fold increase in circulating EPCs.

Example 11

SDF-1α Enhances EPC Homing in Diabetic Peripheral Cutaneous Wounds

Figure 16:
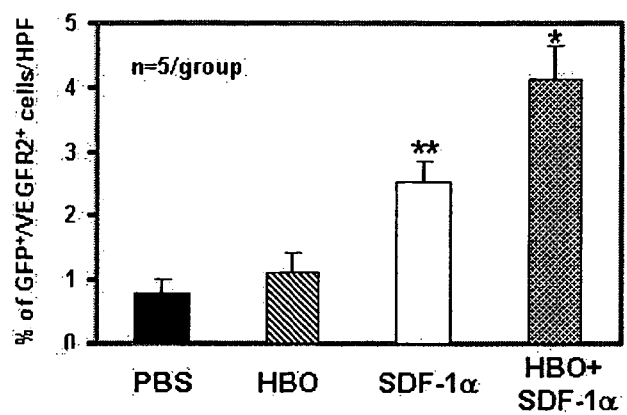
FIG. 16 shows impaired EPC homing to wound tissue in diabetes is reversed by cutaneous administration of SDF-1α. BM cells from GFP/Tg mice were transplanted into γ-irradiated FVB mice. 4 groups of wounded diabetic chimeric mice were treated with daily wound injections of either SDF-1α or PBS±HBO. After 3 d of treatment, wounds were harvested and analyzed by fluorescent immunostaining of tissue sections with anti-GFP-FITC or anti-VEGFR2-PE Abs. Nuclei were counterstained with Hoescht dye. Recruited EPC were identified as GFP$^+$/NEGFR2$^+$cells (yellow). (A) Quantification of recruited EPCs in different groups of diabetic mice. For each animal, 10 random high-power fields (HPF, X100) from 5 serial cross-sections were analyzed and GFP$^+$/VEGFR2$^+$cells was quantified relative to the total wound cellularity. Data are based on 3 experiments. SDF-1α+HBO treated mice had a significant rise in the recruited EPCs compared to other groups (*$P<0.05$). SDF-1α treated animals had a significant increase in tissue EPC compared to PBS control (**$P<0.05$). HBO did not significantly enhance EPC homing to wounds. (B) Representative fluorescent immunostaining of wound sections are shown.
Figure 16:
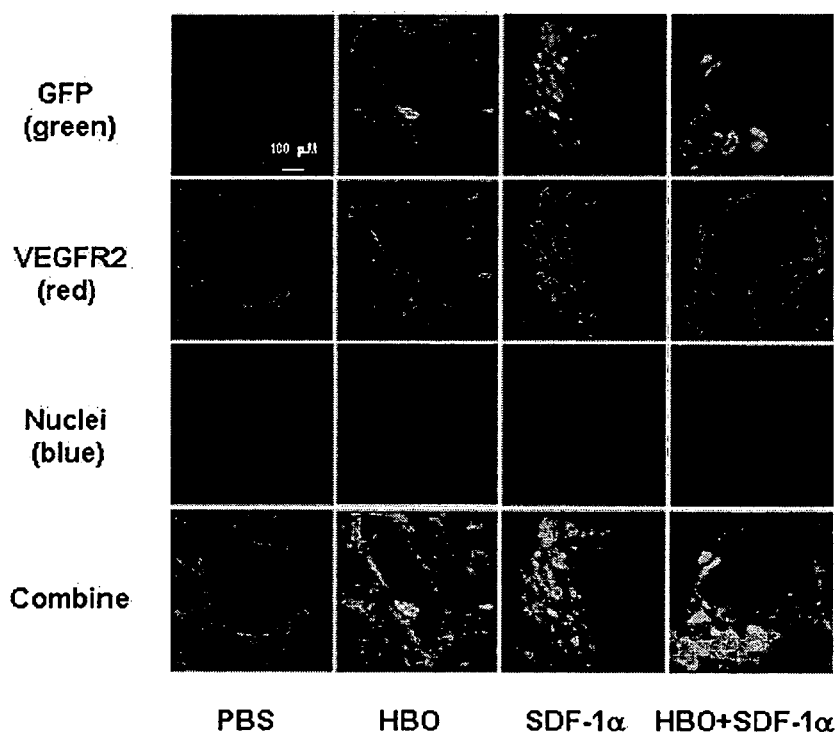

In order to determine the effect of SDF-1α on homing of the hyperoxia-mobilized EPCs to cutaneous wounds, BM transplantation experiments were carried out. After 3 wk, chimeric mice were injected with STZ to induce diabetes and wounds were generated afterwards. Wounded diabetic chimeric mice were treated with both HBO, to mobilize EPCs into circulation, and local wound SDF-1α injections, to correct the observed decreased levels of this homing cytokine in diabetic wounds. It was hypothesized that the combination of these two treatments, by addressing both central systemic release and peripheral homing of EPCs, would result in a synergistic enhancement of EPCs available for recruitment and participation in wound healing. The combination treatment was clearly superior to either modality alone, with HBO not significantly changing the number of EPCs (GFP+/VEGFR2+) present in wound tissue and SDF-1α resulting in a modest, but significant 3-fold increase in wound-level EPCs (FIG. 16). A synergistic 5-fold increase in the number of EPCs was observed in wound tissue of diabetic mice treated with both HBO and SDF-1α compared to untreated diabetic mice. This data indicate that multi-modality therapy aimed at improving both mobilization and homing of EPCs is an effective strategy for significantly impacting the number of EPCs available in wound tissue.

Example 12

Figure 17:
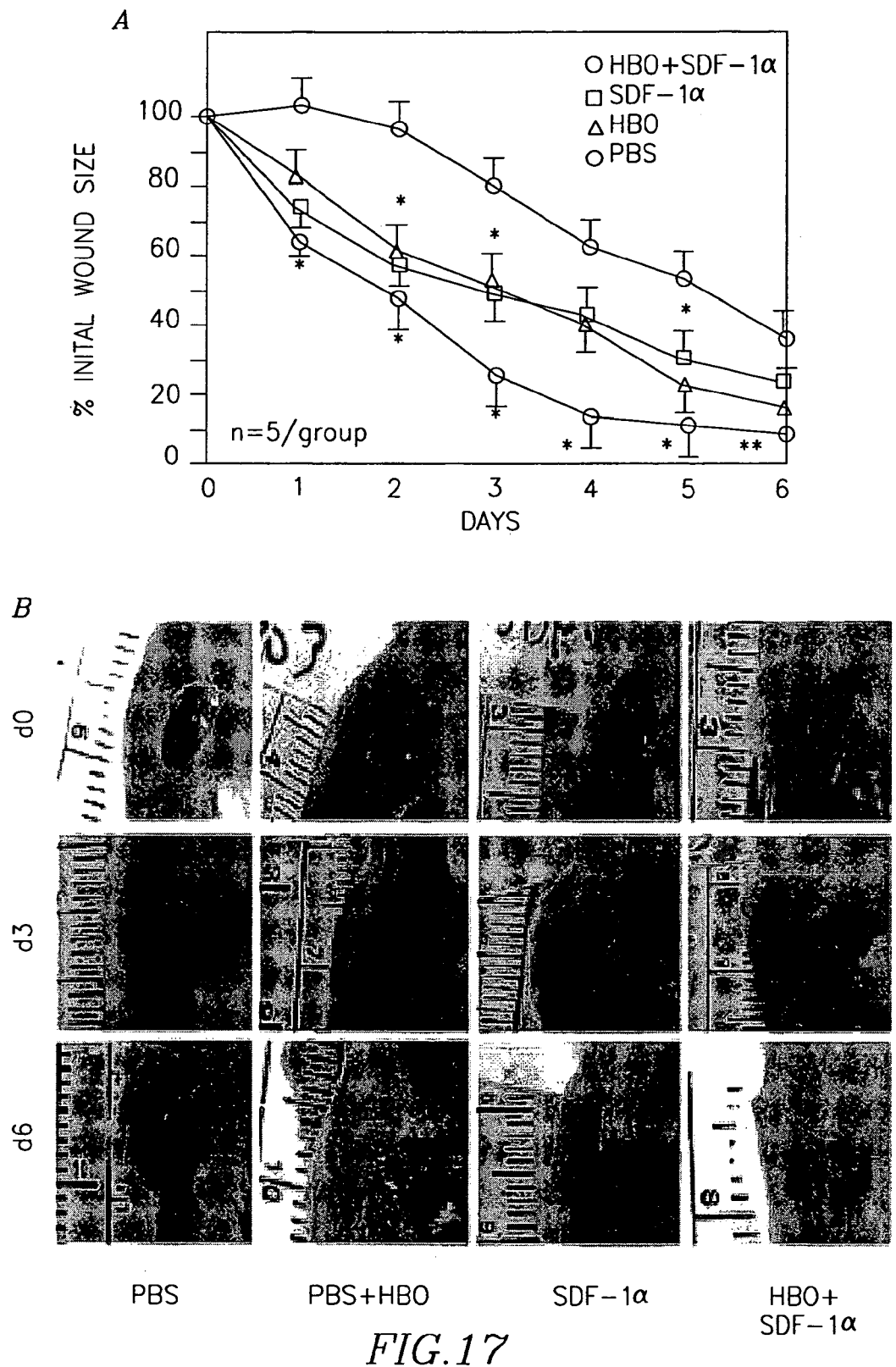
FIG. 17 shows synergistic effect of SDF-1α and HBO on diabetic wound healing. (A) 4 groups of wounded diabetic mice were treated with daily SDF-1α or PBS±HBO. The fraction of initial wound size was measured daily by digital photography and ImageJ analysis for 6 d post-wounding. Each point represents the mean of 5 experiments. Diabetic mice treated with SDF-1α+HBO had significantly improved wound healing rates at all time points when compared with PBS treated controls (*$P<0.001$ at d 1-5, **$P<0.05$ at d 6). Diabetic mice treated with either HBO or SDF-1α demonstrated statistically improved wound healing over PBS controls at d 2, 3 and 5 (*$P<0.05$). (B) Representative wounds at different d are shown for each group. (C) Trichrome staining of wound tissues at d 6. Collagen was stained as blue. (D) Quantification of collagen contents. Data are based on 5 scanned slides in each group at d 6. (E) Blood vessel density in healing wounds. Vessels were stained with anti-VEGFR2-FITC in wounded tissue sections. For each sample, 10 random low-power fields (LPF, X20) from 5 serial cross-sections were analyzed and the number of the vessels was counted. Data are based on 3 experiments. In both (D) and (E), SDF-1α+HBO treated mice had a significant rise in collagen deposit and vessel density (*$P<0.05$) while SDF-1α or HBO treatment had a significant increase compared to PBS control (**$P<0.05$) at d 6 compared to other groups. (F) Effect of timing in the initiation of SDF1α+HBO therapy on wound healing in diabetic mice. Wound closure rates were monitored when treatment is starting at d 0, 1, 3 and 5 post-injure and compared to that in PBS treated group and data were analyzed and presented as described above. Early treatment is necessary.
Figure 17:
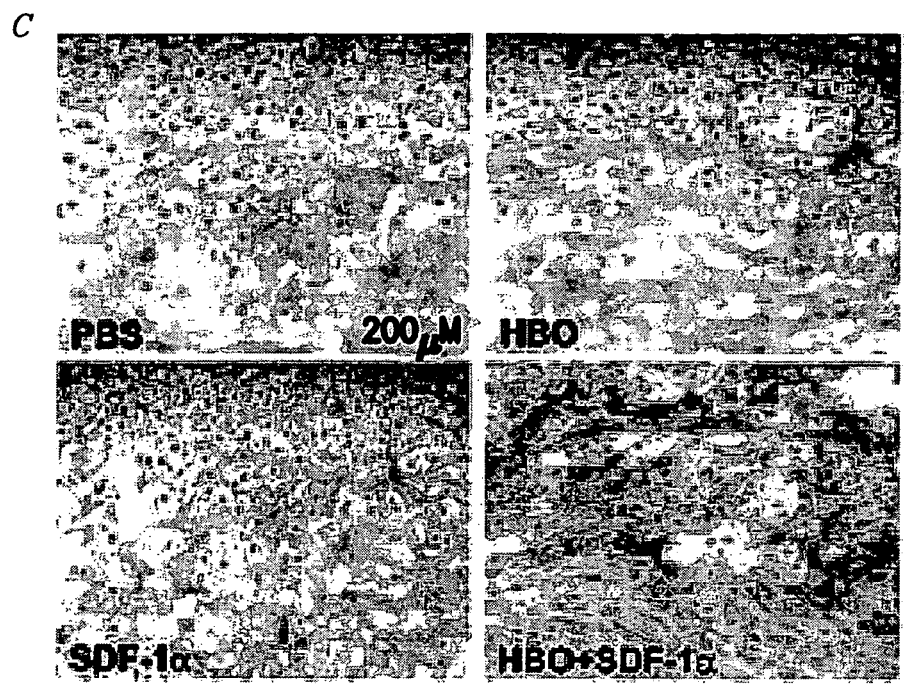
Figure 17:
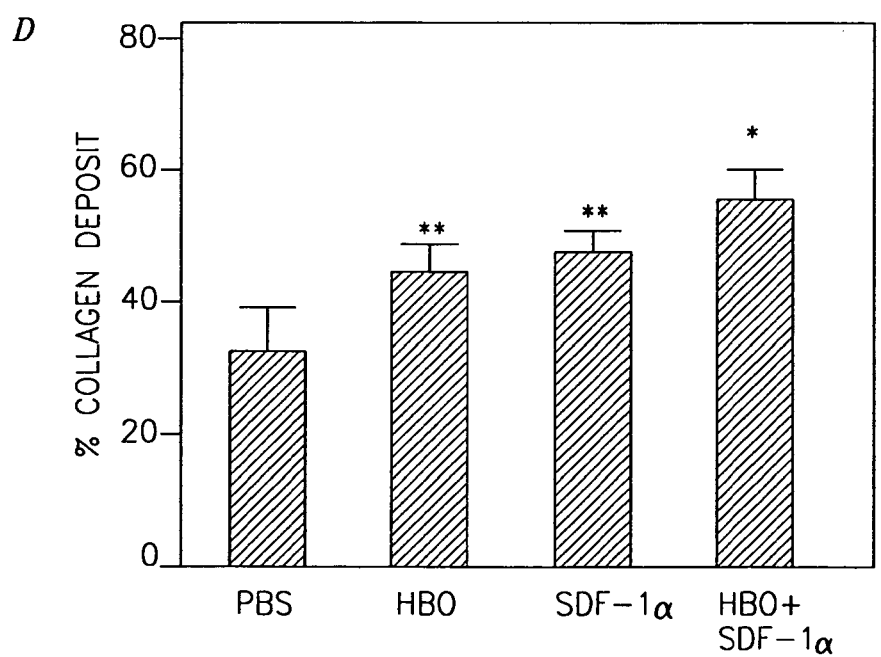
Figure 17:
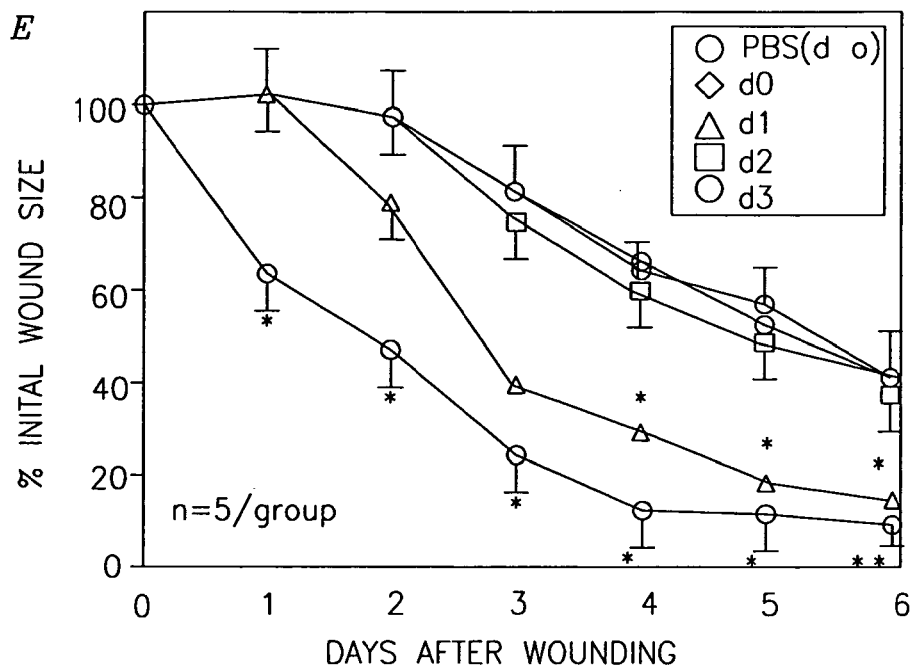

The Combination of Hyperoxia and SDF-1α Significantly Enhances Wound Healing in Diabetic Mice EPCs play a key role in vasculogenesis and cutaneous tissue repair. It was hypothesized that increased numbers of EPCs in circulation, along with enhanced EPC homing to wounds, results in improved wound healing in diabetes. Diabetic wound closure rates were studied, in response to treatment with HBO and SDF-1α alone and in combination. Wounded diabetic mice underwent daily wound injections with SDF-1α, PBS, HBO, or SDF-1α+HBO treatments. Only 3 days after initial injury, wound area was found to decrease by 75% in the group treated with SDF-1α +HBO, as compared with a 20% decrease in the PBS controls (FIG. 17, A and B). This healing response was greater than the response to either treatment modality alone. In addition, histochemical analysis was conducted to examine blood vessel density (VEGFR2 staining), cellularity and stromagenesis (H&E staining), and extracellular constitution (trichrome staining) in wound tissues. Compared with treatment with either HBO or SDF-1α, combined HBO+SDF-1α therapy substantially promoted angiogenesis and stromagenesis and the deposition of collagen in the granulation tissue (FIG. 17, C and D). These data provide substantial evidence to support the synergistic effect of HBO+SDF-1α therapy on accelerating diabetic wound healing. Overall, the data supports the conclusion that these therapies used in concert result in accelerated cutaneous wound healing in diabetic mice. To determine the effect of timing in the initiation of HBO+SDF-1α therapy on wound healing in diabetic mice, wound closure rates were examined, when HBO+SDF-1α treatment was initiated on days 0, 1, 3, and 5 following wounding. Results show that in order to influence wound healing, early application of HBO+SDF-1α is necessary, as initiation of treatment either at initial wounding or 1 day after wounding is effective, while delayed treatment (day 3 or 5) results in the loss of accelerated wound closure rates (FIG. 17E).

Example 13

Insulin is Insufficient to Restore Impaired Diabetic Wound Healing

Figure 18:
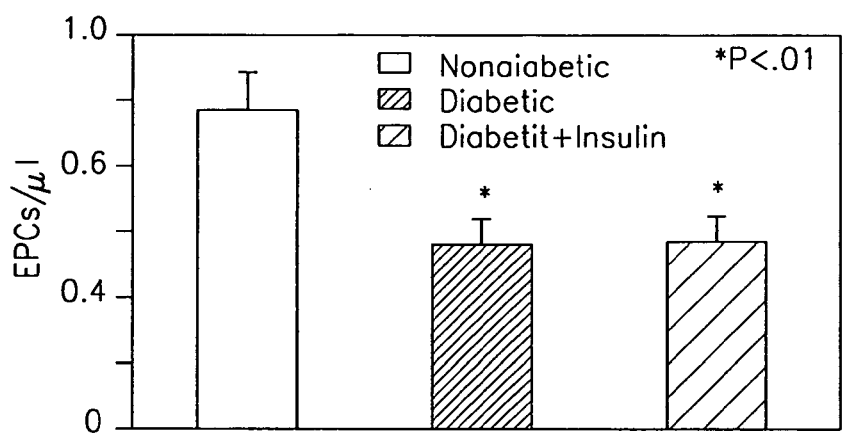
FIG. 18 shows how insulin does not increase EPC mobilization and wound healing in diabetic mice. (A) Quantification of circuiting EPCs by flow cytometry. Data are based on 3 experiments. (B) Representative dot plots are shown. (C) Little effect of insulin on wound healing rate in PBS or HBO+SDF-1α treated diabetic mice (n=10 in each group). Data are based on 2 experiments. No significance was observed when insulin was applied in each pair.
Figure 18:
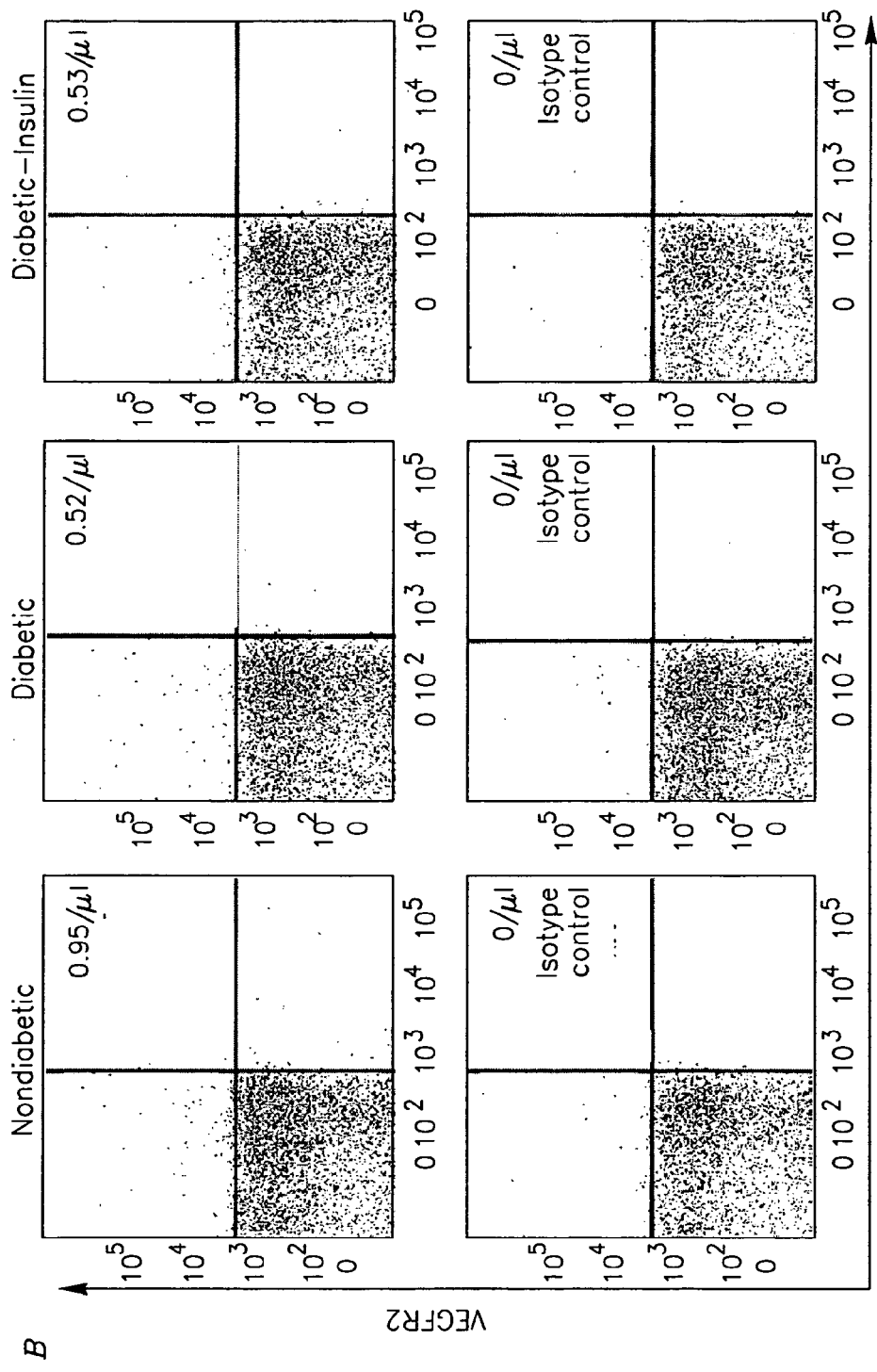
Figure 18:
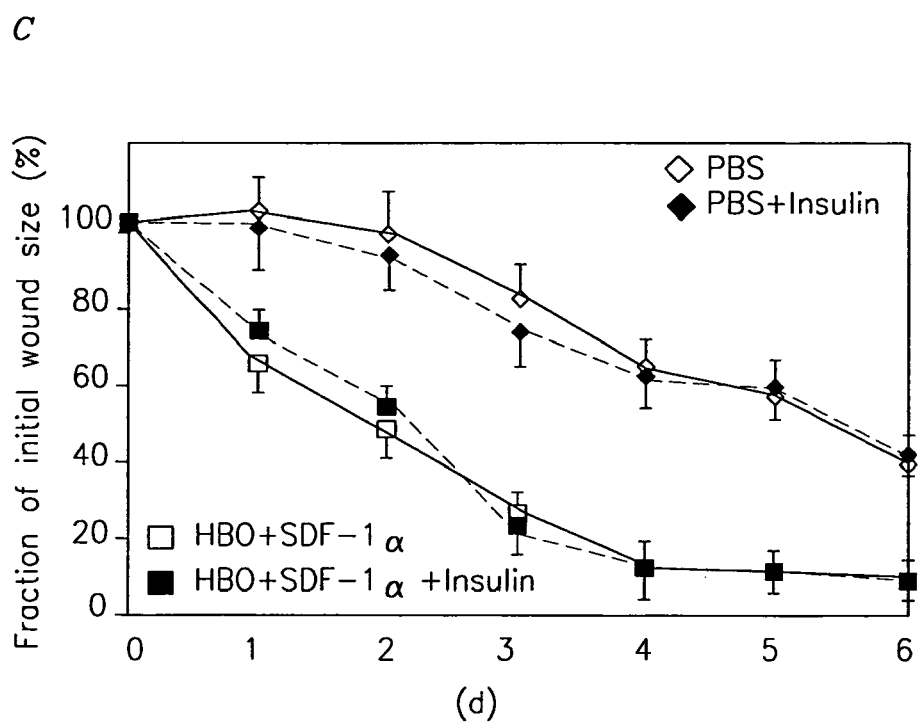

As insulin is a standard therapy to type I diabetes, the effect of insulin on impaired eNOS/NO/EPC mobilization/wound healing in diabetic mice was examined. STZ-induced diabetic mice were treated with insulin (6 U/kg of human insulin (NPH) twice/d) for the duration of each experiment by i.p. injection. The mice with therapeutic euglycemia (glucose <200 mg/dL) were subjected for the subsequent analyses. Interestingly, insulin alone had little effect in reversing impaired BM eNOS phosphorylation (FIG. 10A), BM NO production (FIG. 10D), EPC mobilization (FIG. 18A-B) in diabetic mice. Correspondingly, insulin treatment failed to improve impaired wound SDF-1α production and wound healing rates (FIG. 18C). When combined with HBO+SDF-1α therapy, insulin treatment did not further accelerate the wound healing rate. Our data indicate that short-term insulin treatment has little effects on improvement of diabetic wound healing.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of increasing endothelial progenitor cell numbers (EPC) in a wound of a subject, comprising: mobilizing endothelial progenitor cells by exposing the wound to a hyperbaric, oxygen-enriched atmosphere; and homing the endothelial progenitor cells into the wound by contacting the wound with a composition comprising an endothelial progenitor cells (EPC) homing chemokine, wherein the homing chemokine is SDF-1α, thereby increasing EPC numbers in a wound of the subject, wherein the subject is diabetic.

2. The method of claim 1, whereby the hyperbaric oxygen-enriched atmosphere is between about 2.2 to 3.2 ATA.

3. A method of accelerating a wound healing in a subject, comprising increasing release of endothelial progenitor cells from a bone marrow of said subject by exposing the wound to a hyperbaric, oxygen-enriched atmosphere, and attracting the endothelial progenitor cells into the wound by contacting the wound with a composition comprising an endothelial progenitor cells (EPC) homing chemokine, wherein the homing chemokine is SDF-1α, thereby accelerating a wound healing in the subject, wherein the subject is diabetic.

4. The method of claim 3, wherein the hyperbaric oxygen-enriched atmosphere is between about 2.2 to 3.2 ATA.

5. A method of accelerating a wound healing in a subject, comprising increasing release of endothelial progenitor cells from a bone marrow of said subject by exposing the wound to a hyperbaric, oxygen-enriched atmosphere, and attracting the endothelial progenitor cells into the wound by contacting the wound with a composition comprising an endothelial progenitor cells (EPC) homing chemokine, wherein the homing chemokine is SDF-1α, thereby accelerating a wound healing in the subject, wherein the wound is secondary to a diabetic ischemia.

6. The method of claim 5, whereby said method results in closure of the wound wherein the hyperbaric oxygen-enriched atmosphere is between about 2.2 to 3.2 ATA.

7. A method of increasing endothelial progenitor cell numbers (EPC) in a wound of a subject, comprising: mobilizing endothelial progenitor cells by exposing the wound to a hyperbaric, oxygen-enriched atmosphere; and homing the endothelial progenitor cells into the wound by contacting the wound with a composition comprising an endothelial progenitor cells (EPC) homing chemokine, wherein the homing chemokine is SDF-1α, thereby increasing EPC numbers in a wound of the subject, wherein the wound is secondary to a diabetic ischemia.

8. The method of claim 7, whereby wound healing comprises closure of the wound wherein the hyperbaric oxygen-enriched atmosphere is between about 2.2 to 3.2 ATA.

* * * * *